United States Patent [19]

Hayano et al.

[11] Patent Number: 4,889,998
[45] Date of Patent: Dec. 26, 1989

[54] APPARATUS WITH FOUR LIGHT DETECTORS FOR CHECKING SURFACE OF MASK WITH PELLICLE

[75] Inventors: Fuminori Hayano, Fujisawa; Kazunori Imamura, Tokyo; Sunao Murata, Kawasaki; Kinya Kato, Tokyo, all of Japan

[73] Assignee: Nikon Corporation, Tokyo, Japan

[21] Appl. No.: 148,691

[22] Filed: Jan. 26, 1988

[30] Foreign Application Priority Data

| Jan. 29, 1987 | [JP] | Japan | 62-17155 |
| Feb. 25, 1987 | [JP] | Japan | 62-42247 |
| May 12, 1987 | [JP] | Japan | 62-115649 |
| May 18, 1987 | [JP] | Japan | 62-119079 |

[51] Int. Cl.$^4$ .............. G01N 21/88; G01N 21/32
[52] U.S. Cl. ................... 250/563; 250/572; 356/237
[58] Field of Search ........... 250/572, 563, 562, 209, 250/571; 356/237, 239

[56] References Cited

U.S. PATENT DOCUMENTS

| 4,172,666 | 10/1979 | Clarke | 250/563 |
| 4,468,120 | 8/1984 | Tanimoto et al. | 356/237 |
| 4,541,715 | 9/1985 | Akiyama et al. | 250/572 |
| 4,610,541 | 9/1986 | Tanimoto et al. | 356/237 |
| 4,669,875 | 6/1987 | Shiba et al. | 250/572 |
| 4,731,855 | 3/1988 | Suda et al. | 356/237 |
| 4,776,693 | 10/1988 | Imamura et al. | 356/237 |

OTHER PUBLICATIONS

Akikazu Tanimoto et al, "Proceedings of SPIE", pub. 1984, vol. 470, pp. 242-249.

*Primary Examiner*—Edward P. Westin
*Assistant Examiner*—Michael Messinger
*Attorney, Agent, or Firm*—Shapiro and Shapiro

[57] ABSTRACT

An apparatus for detecting foreign particles on a transparent pellicle comprises a first illuminating device having a first optical axis crossing a surface of the pellicle at a predetermined angle for supplying a light beam onto said transparent pellicle along said first optical axis and a second illuminating device having a second optical axis crossing the surface of said pellicle at an angle different from said predetermined angle for supplying a light beam to said transparent pellicle along said second optical axis. The apparatus further includes a detector for comparing quantity of light of a light beam scattered by a foreign particle and directed to a predetermined direction from said first illuminating device with quantity of light of a light beam scattered by the foreign particle and directed to a predetermined direction from said second illuminating device and for determining a surface of the transparent pellicle on which said foreign particle exists.

9 Claims, 18 Drawing Sheets

EPI-ILLUM

OBLIQUE ILLUM

APPARATUS WITH FOUR LIGHT DETECTORS FOR CHECKING SURFACE OF MASK WITH PELLICLE

BACKGROUND OF THE INVENTION

1. Field of the Invention

The present invention relates to an apparatus for checking defects involved or residing in a mask and/or reticle used for the manufacture of semi-conductor elements, and, in particular, for detecting foreign particles stuck to the mask and/or reticle. More specifically, the present invention relates to an apparatus for checking a mask and/or reticle covered with a transparent film or pellicle to protect the mask and/or reticle against fine dust floating in the environment, or the transparent film or pellicle itself.

2. Related Background Art

Apparatuses for automatically detecting foreign particles stuck to a mask and/or reticle (referred to generically as "reticle" hereinafter) by scanning the reticle by means of light beams are already known, as disclosed in the U.S. Pat. Nos. 4,468,120 and 4,610,541. Such conventional apparatus checks the existence of the foreign particles, size of the particles and sticking condition of the particles, by linearly scanning a surface of the reticle in x-direction by means of a galvano-mirror (vibration mirror) and the like, while directing a spot of condensed laser beam onto said surface at an incident angle of 10° to 20°, by shifting the reticle in y-direction, and then by receiving the light scattered laterally and rearwardly (among the reflected light) by means of a plurality of photoelectric detectors arranged in a space position related specially with respect to the position of illumination of the laser beam.

In such checking apparatuses, it has recently been desirable to enable effective checking of a reticle with a thin film of polymeric material (referred to as "pellicle" hereinafter).

The pellicle is fixedly supported on the reticle by a supporting frame so that the pellicle covers the reticle leaving a space between the pellicle and a surface of the reticle, thereby preventing adhesion or sticking of the foreign particles on the reticle. When a projecting and exposing operation is performed by means of an exposing device making use of such pellicle, even if the foreign particles are stuck or adhered to the surface of the pellicle, an image of the foreign particles is not transferred onto a semi-conductor wafer which receives projected images, since the image of the foreign particles is not focused on the wafer.

However, when the size of the foreign particles stuck to the surface of the pellicle is relatively large, there would be patches on the semi-conductor wafer (uneven exposure). Further, when some of the foreign particles stuck to a lower surface of the pellicle (i.e., a surface facing the reticle) drop from the surface of the pellicle onto the reticle, even if they are not so large as to create uneven exposure, the image of the dropped particles would be transferred to the semi-conductor wafer.

Therefore, even if the pellicle is used, it is necessary to check or inspect the position and size of the foreign particles stuck to the pellicle, and further to judge or discriminate whether the foreign particles are stuck to an upper surface (remote from the reticle) of the pellicle or a lower surface (facing the reticle) of the pellicle. However, such discrimination could not be obtained by the conventional checking apparatuses.

Further, when the reticle covered with the pellicle was checked by the conventional apparatuses without any additional devices, the inventors of the present invention have found the following disadvantages.

Firstly, since the laser beam or light advances obliquely from the pellicle to the reticle, an incident angle of the laser beam would be changed in accordance with the scanning positions, thereby changing light intensity of the spot of the laser beam reaching the reticle surface, due to the fact that light permeability of the pellicle is seemingly changed by the change of the incident angle of the laser beam with respect to the pellicle.

Secondly, since the photoelectric detectors are arranged in predetermined space position, an angle formed between the pellicle and a light path of the scattered light sent from the foreign particles to the photoelectric detectors is changed in accordance with the sticking position of the foreign particles, and accordingly the scanning position of the light spot, due to the fact that light permeability of the pellicle is seemingly changed by changing an incident angle of the scattered light with respect to the pellicle.

Accordingly, even if the foreign particle is stuck in the same position, there arises a problem that the sensitivity of the detection of the foreign particle between the reticle with the pellicle and the reticle without the pellicle is different.

Further, since the supporting frame for supporting the pellicle is arranged around a pattern area of the reticle, when the pellicle is mounted on the reticle, there arose a defect that a part of the scattered light from the foreign particles stuck to the reticle is interrupted by the supporting frame so as not to reach the photoelectric detectors. In order to correct the defect, a method in which after the reticle is checked, the reticle is rotated at an angle of 90° or 180°, and then the reticle is checked again can be adopted; however, this method is time consuming, and thus, is not desirable.

Furthermore, in the conventional apparatus for detecting the foreign particles, a light beam having the same diameter has been used both for checking the reticle surface and for checking the pellicle surface.

In general, the sensitivity of the detection of the foreign particle depends upon the beam diameter of the light beam for scanning the surface to which the foreign particle is stuck; the smaller the beam diameter the higher the sensitivity of the detection of the foreign particle, thus enabling the detection of the smaller foreign particle. On the other hand, the smaller the beam diameter, the longer the time for evenly scanning the whole surface to be checked.

As described above, the foreign particles stuck to the pellicle are not easily projected onto the semi-conductor wafer (in comparison with the foreign particles stuck to the reticle), even if the particles are relatively large. In other words, an allowable size of the foreign particle stuck to the reticle differs from that of the pellicle; the pellicle is permitted to have the larger particles than the reticle.

Accordingly, when the pellicle surface is checked by the above-mentioned conventional detecting apparatus, the foreign particles which are smaller than those that need to be detected can also be detected, with the result that there arose a problem that it took longer for the detection of the foreign particles than normally needed.

SUMMARY OF THE INVENTION

A main object of the present invention is to provide an apparatus for checking a mask or reticle provided with a protection film or pellicle, which enables the high accuracy checking of a surface of the protection film or pellicle and/or of a surface of the mask or reticle.

Another object of the present invention is to provide an apparatus for detecting foreign particles stuck to a protection film or pellicle, which can discriminate or determine the position and size of the foreign particles, as well as whether the particles are stuck to an upper surface of the film or pellicle or a lower surface of the film or pellicle.

BRIEF DESCRIPTION OF THE DRAWINGS

FIGS. 12C, 12D, 13E, and 12F are graphs showing correction features of amplification degree;

DESCRIPTION OF THE PREFERRED EMBODIMENTS

The present invention will now be explained with reference to the attached drawings.

First of all, a checking apparatus according to a first embodiment of the present invention will be explained. The checking apparatus according to the first embodiment can discriminate whether foreign particles are stuck to an upper surface of a pellicle or a lower surface of the pellicle, as well as the position and size of the foreign particle.

An explanation will be given with regard to scattered light emitted from the foreign particles, when the foreign particles stuck or adhered to both surfaces of the pellicle are illuminated from different directions.

Figure 1:
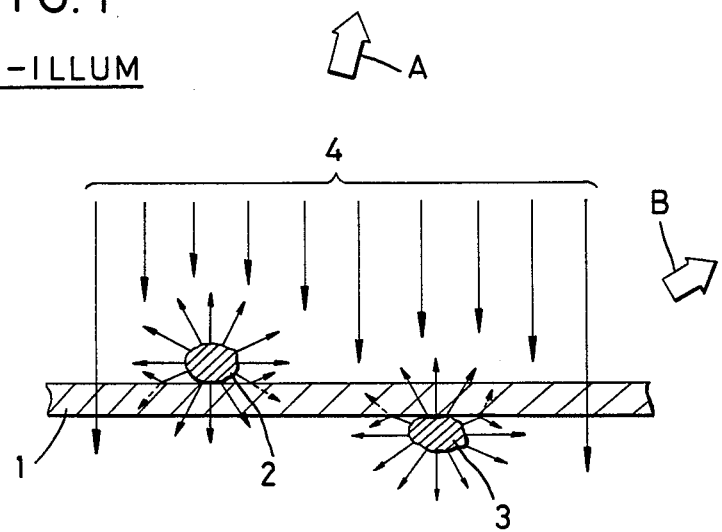
FIGS. 1 and 2 are explanatory views showing scattered light beams from foreign particles when a pellicle undergoes epi-illumination and oblique illumination, respectively.
Figure 2:
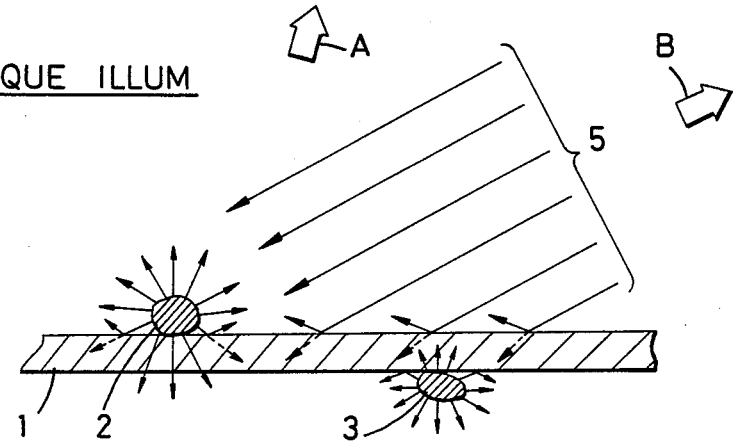

FIGS. 1 and 2 show the condition or appearance of illumination and scattered light from foreign particles when a light-permeable pellicle 1 to upper and lower surfaces of which foreign particles 2 and 3 are stuck is illuminated from different directions.

Particularly, FIG. 1 shows illumination light 4 and scattered light from the foreign particles 2 and 3 when the pellicle 1 is illuminated from a direction that forms a relatively large angle with respect to the plane of the pellicle (referred to as "epiillumination" hereinafter). On the other hand, FIG. 2 shows illumination light 5 and scattered light from the foreign particles when the pellicle 1 is illuminated from a direction that forms a relatively small angle with respect to the plane of the pellicle (referred to as "oblique illumination" hereinafter).

Firstly, the quantity of scattered light emitted from the foreign particles received in a given direction, for example direction A shown in FIGS. 1 and 2 will be comparatively explained with respect to the epi-illumination and oblique illumination.

The quantity of scattered light emitted from the foreign particle 2 stuck to the upper surface of the pellicle 1 under the epi-illumination is substantially the same as that under the oblique illumination, if the quantity of the light of the epi-illumination is substantially the same as that of the oblique illumination. On the other hand, with respect to the foreign particle 3 stuck to the lower surface of the pellicle 1, the quantity of the scattered light from the foreign particle under the oblique illumination is less than that under the epi-illumination, due to the fact that under the oblique illumination, since the illumination light 5 is reflected substantially completely on the upper surface of the pellicle 1, the quantity of light reaching the foreign particle 3 is less than that under the epi-illumination where a large amount of the illumination light passes through the pellicle 1.

Accordingly, it is possible to discriminate whether the foreign particle is stuck to the upper surface of the pellicle or the lower surface thereof, by illuminating the pellicle surface from two different directions and by comparing the quantity of the scattered light from the foreign particle obtained by such illumination from two directions.

Secondly, the quantity of scattered light emitted from the foreign particles received in two different directions, for example directions A and B shown in FIGS. 1 and 2 when the pellicle is illuminated from a given direction will be explained.

With respect to the foreign particle 2 stuck to the upper surface of the pellicle 1, the quantity of the scattered light from the foreign particle 2 received in the direction A is substantially the same as that received in the direction B. On the other hand, with respect to the foreign particle 3 stuck to the lower surface of the pellicle 1, the quantity of the scattered light received in the direction B is less than that received in the direction A, due to the fact that the scattered light directed from the foreign particle 3 to the direction B is almost reflected on the lower surface of the pellicle 1.

Accordingly, it is possible to discriminate whether the foreign particle is stuck to the upper surface of the pellicle or the lower surface thereof, by illuminating the pellicle from a given direction, by receiving the scattered light from the foreign particle in two different directions and by comparing the quantity of the received light in said two directions. Further, as shown in FIG. 2, when an incident angle of the illumination light 5 in the oblique illumination is so selected that the illumination light 5 is totally reflected on the pellicle surface, if there is no foreign particle stuck to the upper surface of the pellicle, since the oblique illumination light 5 is totally reflected on the upper surface of the pellicle and the scattered light from the foreign particle 3 stuck to the lower surface of the pellicle is also totally reflected on said lower surface, the difference in the quantity of light between the scattered light directed to the direction A in FIG. 1 and that directed to the direction B can be more precisely clarified, which is desirable for the detection of the foreign particles.

Figure 3:
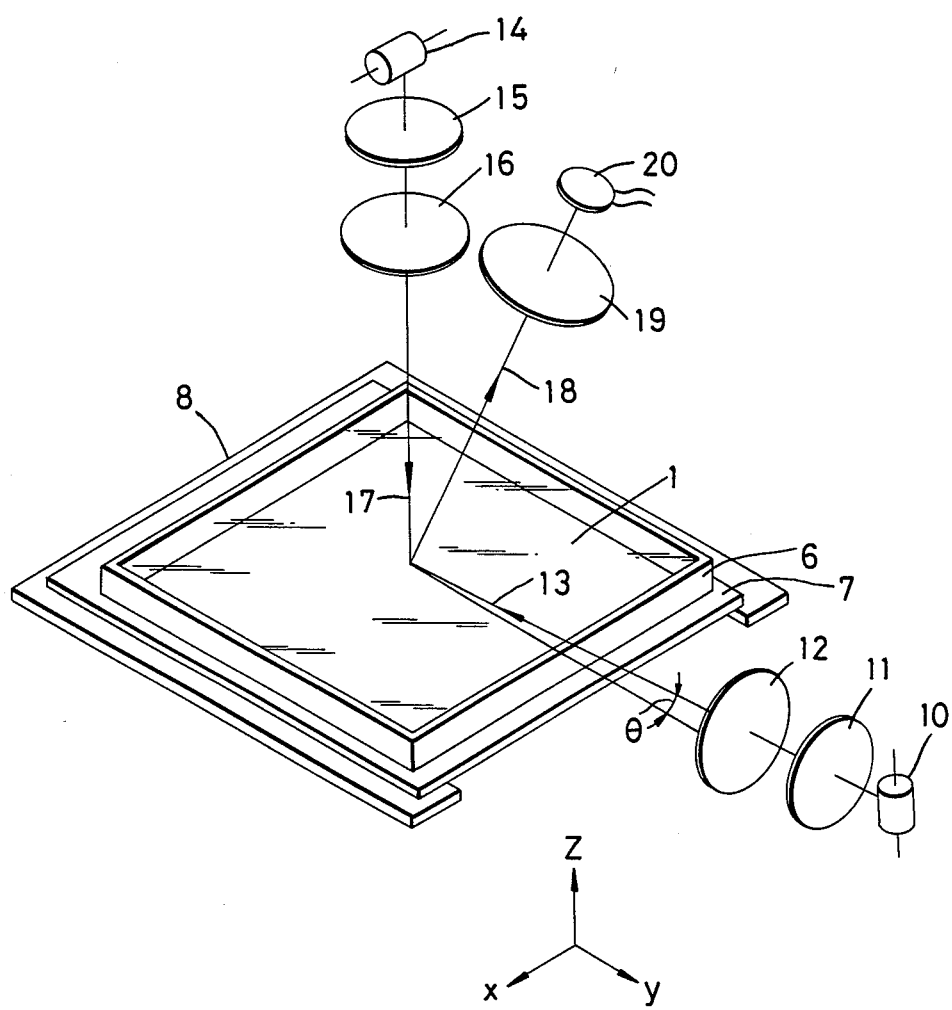
FIG. 3 is a perspective view showing a checking apparatus according to a first embodiment of the present invention.

In FIG. 3, the pellicle 1 is supported by a supporting frame 6 resting on a base plate 7 for the reticle or mask. The base plate 7 is fixed on a stage 8 which can be shifted independently to x-direction and y-direction in the illustrated x-y-z co-ordinate system by means of a motor (not shown).

A light source 10 for the oblique illumination is arranged laterally of the pellicle 1 and a light source 14 for the epi-illumination is arranged above the pellicle. These light sources 10 and 14 may be sources used with a conventional microscope and the like.

Light emitted from the light source 10 is converted to a substantially collimated light beam by means of a lens 11 and then illuminates the pellicle 1 through a filter 12 through which a quantity of light is controlled. Similarly, light emitted from the light source 14 is also converted to a substantially collimated light beam by a lens 15 and then illuminates the pellicle through a filter 16 through which a quantity of light is controlled.

A photoelectric detector 20 is arranged above the pellicle 1 and obliquely with respect to the pellicle. Scattered light emitted from the foreign particle is condensed by a lens 19 and is received by the photoelectric detector 20, where the received light is converted to an electric signal in proportion to the quantity of the received light.

An angle $\theta$ between the plane of the pellicle 1 and an optical axis 13 of the light from the light source 10 is selected in the order of 0° to 10°. On the other hand, an angle between the plane of the pellicle 1 and an optical axis 17 of the light from the light source 14 may be relatively larger than the above-mentioned angle $\theta$ regarding the optical axis 13, and in practice may be selected in the order of 20° or more.

It should be noted that both of the light sources 10 and 14 are not necessarily arranged on the same side of the pellicle 11 for example, the light source 14 can be arranged below the pellicle 1 or at the side opposite to the light source 10 of the oblique illumination.

An optical axis 18 of the photoelectric detector 20 is so arranged that the detector 20 receives the scattered light from the foreign particle in the so-called dark field illumination by angularly deviating the optical axis 18 from both the optical axes 13, 17 and optical axes of light beams regularly reflected on the pellicle and emitted from the light sources 10 and 14.

In operation, at first, the quantity of light reaching the pellicle surface from the light sources 10 and 14 is previously adjusted by means of the filters 12 and 14 for adjusting the quantity of light in such a manner that the quantity of the scattered light received by the photoelectric detector 20 and emitted from the foreign particle stuck to the upper surface (illuminated surface) of the pellicle under the epi-illumination is exactly the same as that under the oblique illumination (that is to say, an output voltage of the photoelectric detector 20 obtained by receiving the scattered light from the foreign particle under the epi-illumination is the same as that under the oblique illumination). With respect to the illumination operation, for example, the epi-illumination is firstly effected alone, thereby detecting the scattered light from the foreign particle under the epi-illumination by means of the photoelectric detector 20. Thereafter, the oblique illumination is effected alone, thereby detecting the scattered light from said foreign particle under the oblique illumination. By repeating such illumination operations alternately for a predetermined period and by comparing the variation in the obtained photoelectric signals, it is possible to discriminate whether the foreign particles are stuck to the upper surface of the pellicle or the lower surface thereof.

As to the above-mentioned illumination operations in which the epi-illumination and the oblique illumination are effected independently or separately, one of the light sources may be deenergized or extinguished while energizing the other light source. Alternatively, both of the light sources can be continuously energized or lighted, but shutters can be provided on the optical axes of the light sources so that only the light beam from one of the light sources reaches the pellicle by opening and closing the shutters selectively.

Next, features of the photoelectric signals obtained from the photoelectric detector 20 will be explained with reference to FIG. 4.

Figure 4:
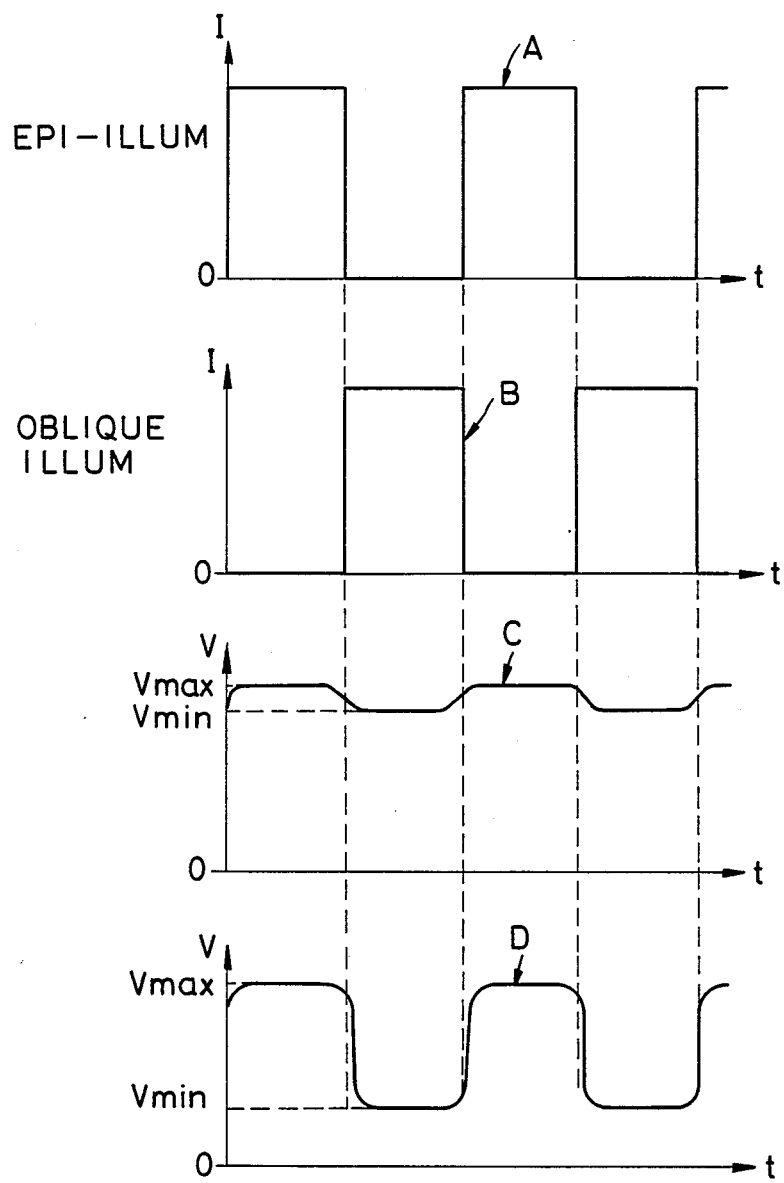
FIG. 4 shows outputs from a photoelectric detector.

FIG. 4 shows Variation A of "light intensity" I regarding "time" when the epi-illumination is effected by means of the light source 14; Variation B of "light intensity" I regarding "time" when the oblique illumination is effected by the light source 10; Variation C of the "photoelectric voltage" V regarding "time" when the photoelectric detector 20 receives the scattered light from the foreign particle 2 stuck to the upper surface (illuminated surface) of the pellicle; and Variation D of the "photoelectric voltage" V regarding "time" when the photoelectric detector 20 receives the scattered light from the foreign particle 3 stuck to the lower surface of the pellicle 1, respectively.

When the epi-illumination and the oblique illumination are repeated alternately at a predetermined cycle, as shown in the Variation C, variation or change (Vmax−Vmin) in the scattered light emitted from the foreign particle stuck to the upper surface of the pellicle will be substantially zero. On the other hand, as shown in the Variation D, variation or change (Vmax−Vmin) in the scattered light emitted from the foreign particle stuck to the lower surface of the pellicle will be relatively larger than that in the Variation C; in this case, if the incident angles of the light beams from the light sources are appropriately selected, Vmin may be in the order of 50% or less of Vmax.

Therefore, by comparing the difference in the variation or change of the photoelectric voltages, it is possible to determine the sticking direction of the foreign particle, and thus, to discriminate whether the foreign particle is stuck to the upper surface of the pellicle or the lower surface thereof. More particularly, for example, it is possible to determine the fact that the foreign particle is stuck to the upper surface of the pellicle 1 when a standardized value (Vmax−Vmin)/(Vmax+Vmin) is less than a predetermined value (for example, 0.33) and to determine the fact that the foreign particle is stuck to the lower surface of the pellicle when said standardized value is equal to said predetermined value or more. Further, a rough size of the foreign particle can be judged from the value of Vmax.

Next, means for treating the outputs emitted from the photoelectric detector 20 will be explained with reference to FIGS. 5 and 6.

Figure 5:
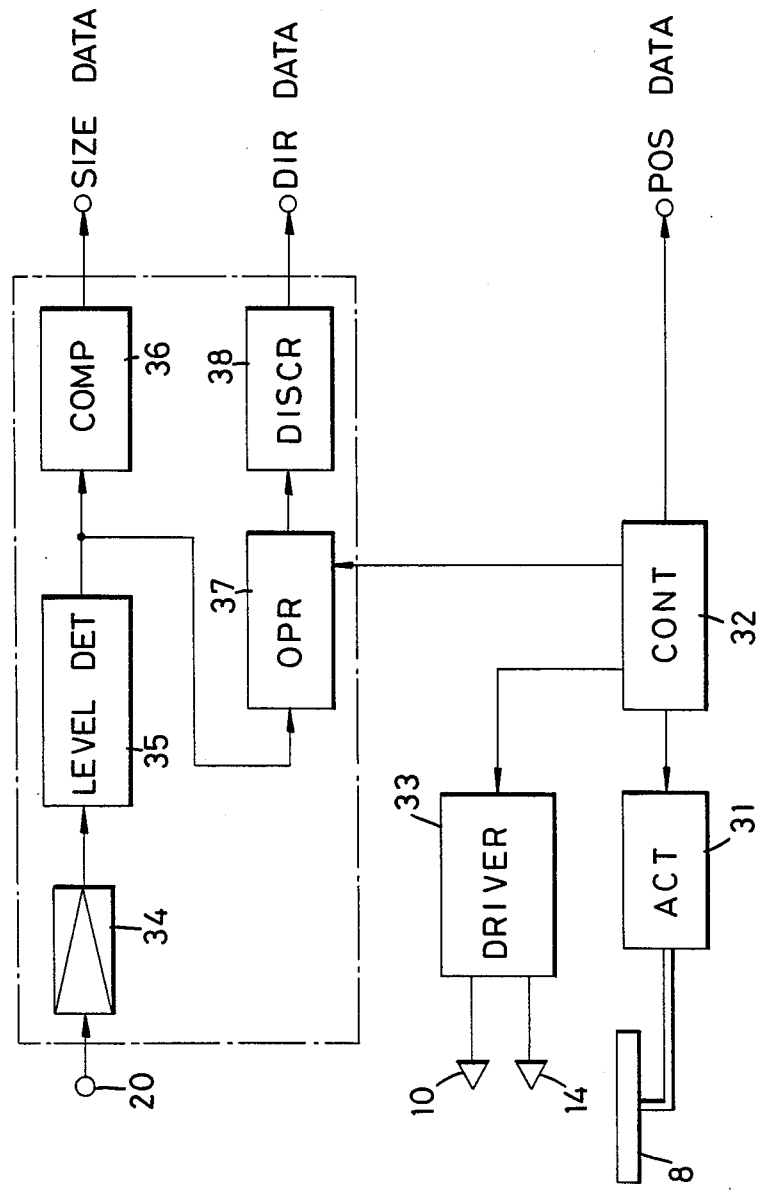
FIG. 5 is a circuit block diagram of means for treating or conducting the outputs from the photoelectric detector.
Figure 6:
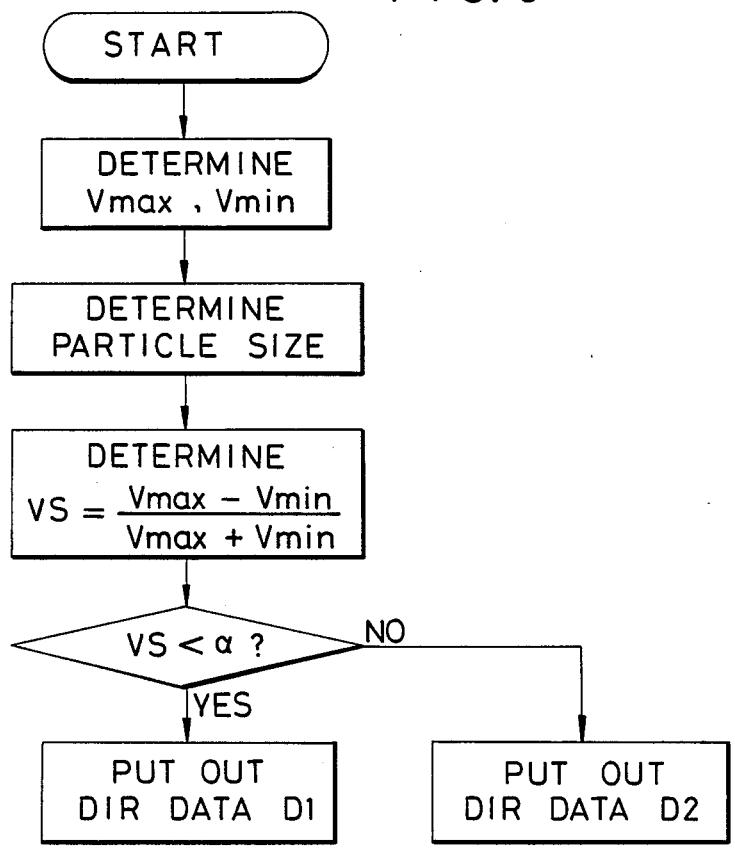
FIG. 6 shows a flow chart showing a main operation in the checking apparatus according to the first embodiment of the present invention.

FIG. 5 shows an example of construction of said treating means. In FIG. 5, an actuator 31 for shifting the stage 8 is controlled by a controller 32. The above-mentioned light sources 10 and 14 can be energized alternately by means of a driver 33 controlled by the controller 32. The photoelectric detector 20 is connected, through an amplifier 34, to a level detector 35 which can detect both the above-mentioned maximum value Vmax and the minimum value Vmin. An output from the level detector 35 is supplied to a comparator 36 and to an operator 37. In the comparator 36, inputted data are compared with base data which have previously been statistically obtained and stored in the comparator and which represent the relationship between the sizes of the foreign particles and the photoelectric voltages, thereby forming "size data" representing a rough size of each of the foreign particles.

On the other hand, in the operator 37, operations for finding out the sum (Vmax+Vmin) and the difference (Vmax−Vmin) of the maximum value Vmax of the photoelectric voltage and the minimum value Vmin thereof are effected.

An output of the operator 37 is connected to a discriminator 38. In this discriminator 38, the abovementioned standardized value (Vmax−Vmin)/(Vmax+Vmin) is found out, and a magnitude relationship between said standardized value and a pre-set criterion value α is judged. It should be noted that said criterion value α is not limited to a specific value; for example, as explained with reference to FIG. 4, said value α may be in the order of 0.33. If the above-mentioned standardized value (Vmax−Vmin)/(Vmax+Vmin) regarding a variation in the quantity of light is smaller than the criterion value α, it is judged or discriminated that the foreign particle is stuck to the upper surface of the pellicle 1, and if the standardized value is equal to or more than the criterion value α, it is discriminated that the foreign particle is stuck to the lower surface of the pellicle. The discriminator 38 outputs "direction data" which represent a sticking direction of the foreign particle against the pellicle (i.e., represent the upper or lower surface to which the foreign particle is stuck). The controller 32 effects a necessary control relative to each of the above portions and generates positional data showing a position of a stage 8.

Next, an operation of the afore-mentioned means for treating the photoelectric signals from the photoelectric detector 20 will be explained with reference to a flow chart shown in FIG. 6. FIG. 6 shows an operation when the output signal is emitted from the photoelectric detector.

Firstly, controlling instructions from the controller 32 are applied to the driver 33, thereby energizing the light sources 10 and 14 alternately. Next, other controlling instructions from the controller 32 are applied to the actuator 31, thereby shifting the stage 8 in such a manner that the scanning of the pellicle 1 by means of the light beam is effected at a speed slower than a period of the energization-deenergization cycle of the light sources 10 and 14.

If the foreign particle is stuck or adhered to the pellicle, the scattered light from said foreign particle is received by the photoelectric detector 20. The output voltage or photoelectric voltage from the photoelectric detector 20 is amplified by the amplifier 34 and then is sent to the level detector 35, where the maximum value Vmax and the minimum value Vmin are found out. Among these values, the maximum value Vmax is inputted or supplied to the comparator 36, where said maximum value is compared with the base data which have previously been statistically obtained and which represent the relationship between the sizes of the foreign particles and the photoelectric voltages (photoelectric signals), thereby finding out a rough size of said foreign particle.

Next, the maximum value Vmax and the minimum value Vmin found out in the level detector 35 are inputted to the operator 37, where the sum (Vmax+Vmin) and the difference (Vmax=Vmin) of these values are found out.

These found values are inputted to the discriminator 38, where the standardized value regarding the variation in the quantity of light VS (=(Vmax−Vmin)/(Vmax+Vmin)) is found out. And, it is discriminated whether the standardized value VS is smaller than the criterion value α or not. If the standardized value VS is smaller than the criterion value α, the discriminator 38 generates direction data D1 which represent that the foreign particle is stuck to the upper surface of the pellicle, and if the standardized value VS is equal to or more than the criterion value α, the discriminator 38 generates direction data D2 which represent that the foreign particle is stuck to the lower surface of the pellicle.

On the other hand, positional data of the detected foreign particle regarding x-y directions on the pellicle are outputted from the controller 32.

Figure 7:
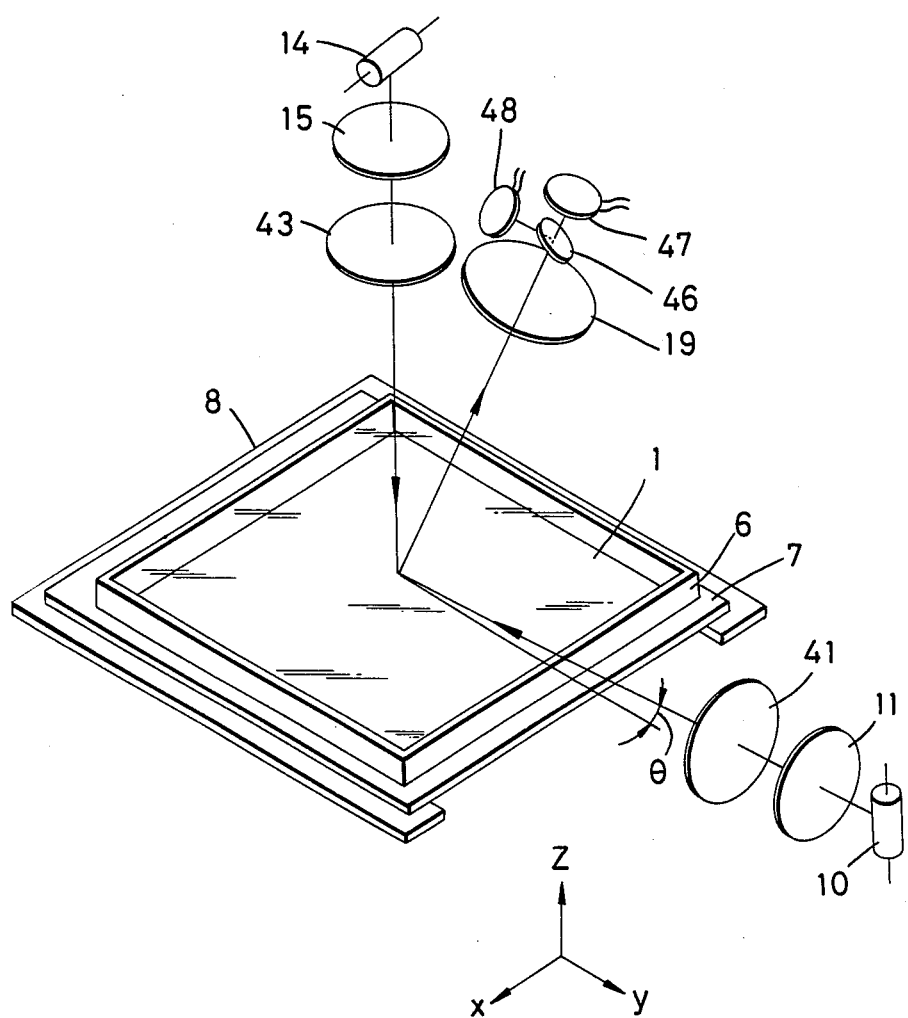
FIG. 7 is a perspective view showing a modification of the first embodiment.

In place of the above-mentioned embodiment in which two light sources 10 and 14 are energized alternately, a modification in which the wavelength of the light from the light source 10 differs from the wavelength of the light from the light source 14 thereby detecting the scattered light emitted from the foreign particle on the basis of the wavelengths may be adopted. An example of such modification is shown in FIG. 7. In this example, wavelength selecting filters 41 and 43 are provided in place of the filters 12 and 16 in FIG. 3. Further, in place of the photoelectric detector 20, two photoelectric detectors 47 and 48 are provided, and a wavelength discriminating filter 46 such as a dichroic filter is interposed between the detectors 47, 48 and the lens 19.

An example of a method for selecting or distinguishing the light on the basis of the wavelength of the light by means of the above arrangement will be explained.

For example, the wavelengths of the light from the light sources 10 and 14 are adjusted, by the wavelength selecting filters 41 and 43, in such a way that the light from the light source 14 can pass through the wavelength discriminating filter 46 but the light from the light source 10 is reflected on the filter 46. With such adjustment, the scattered light from the foreign particle created by the light emitted from the light source 14 can be detected by the photoelectric detector 47 but cannot be detected by the photoelectric detector 48; on the other hand, the scattered light from the foreign particle created by the light emitted from the light source 10 can be detected by the photoelectric detector 48 but cannot be detected by the photoelectric detector 47. With respect to the scattered light from the foreign particle stuck to the upper surface of the pellicle 1, the output voltage from the photoelectric detector 47 is substantially the same as the output voltage from the photoelectric detector 48. On the other hand, with respect to the scattered light from the foreign particle stuck to the lower surface of the pellicle 1, the level of the output voltage from the photoelectric detector 48 is less than that from the photoelectric detector 47.

Therefore, when the output voltage from the photoelectric detector 47 is S(47) and the output voltage from the photoelectric detector 48 is S(48), by comparing a value S(47)/S(48) with a predetermined value (for example, 2), it is possible to discriminate whether the foreign particle is stuck to the upper surface of the pellicle or the lower surface of the pellicle. For example, when the value S(47)/S(48) is 2 or more than the predetermined value, it can be judged that the foreign particle is stuck to the lower surface of the pellicle, and when the value S(47)/S(48) is 2 or less than the predetermined value, it can be judged that the foreign particle is stuck to the upper surface of the pellicle.

As described above, it should be understood that, in principle, if the position of the illuminating system is replaced by the position of the photoelectric system (light receiving system), the effects similar to those in the above embodiments can be obtained. A checking apparatus which utilizes the above principle is disclosed in the U.S. Pat. No. 4,468,120.

Next, a modification according to the above replacement will be explained with reference to FIG. 8.

Figure 8:
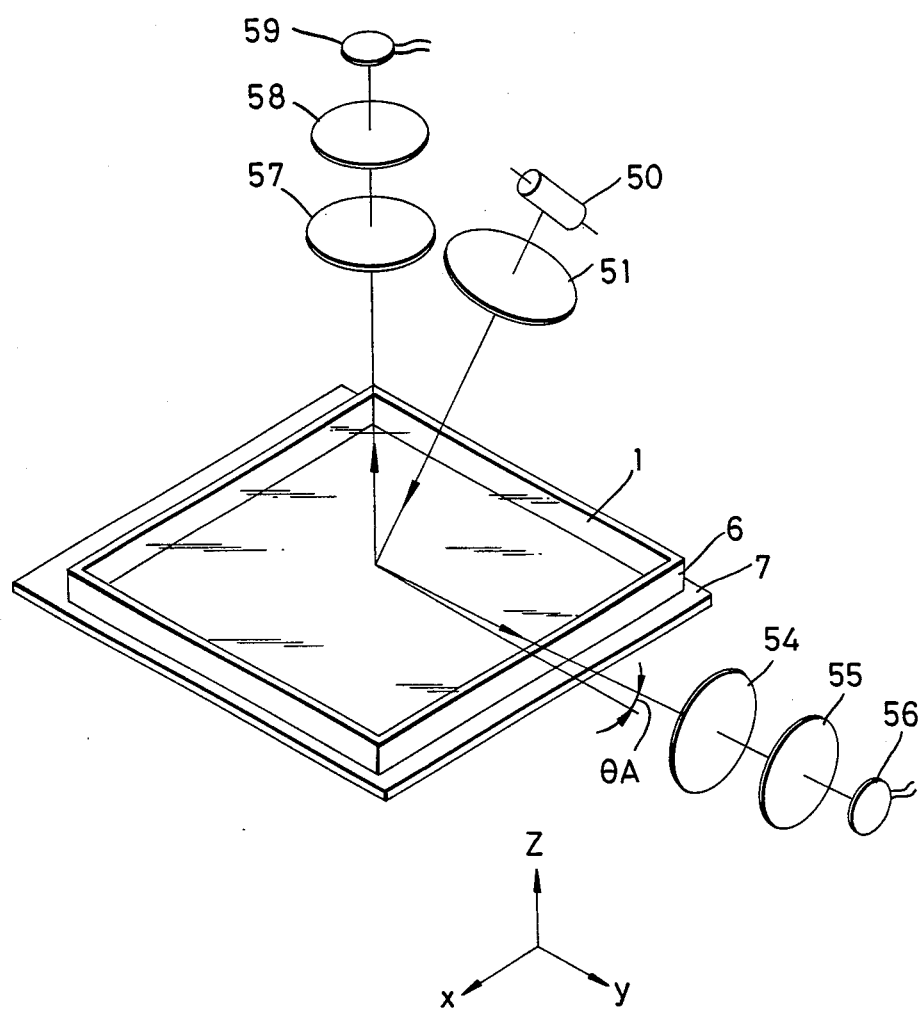
FIG. 8 is a perspective view showing another modification of the first embodiment.

In FIG. 8, the light emitted from a light source 50 illuminates the pellicle 1 through a lens 51. Scattered light from the foreign particle is received by photoelectric detectors 56 and 59 through filters 54, 57 (for adjusting quantity of light) and lenses 55, 58, respectively. The light emitted from the light source 50 is converted to a substantially collimated light beam by means of the lens 51 and then is sent to the pellicle 1 from the above and obliquely. Of course, the oblique illumination as shown in FIG. 2 is preferable.

A light receiving angle of the photoelectric detector 56, i.e., an angle $\theta_A$ formed between the plane of the pellicle and an optical axis of said detector may be substantially the same as the aforementioned angle $\theta$ under the oblique illumination in the first embodiment, and, therefore, may be in the order of 0–10°. Similarly, an angle between the plane of the pellicle 1 and an optical axis of the photoelectric detector 59 may also be substantially the same as the afore-mentioned angle under the epiillumination in the above first embodiment, and thus, may be selected in the order of 20° or more.

In this modification (FIG. 8), since the ratio between the photoelectric output voltages obtained from two photoelectric detectors 56 and 59 when the foreign particle is stuck to the upper surface of the pellicle 1 is substantially different from the corresponding ratio when the foreign particle is stuck to the lower surface of the pellicle, it is possible to determine the surface to which the foreign particle is stuck by comparing said ratios.

More particularly, at first, the filters 54 and 57 for adjusting the quantity of light are so adjusted that the output voltages S(56) and S(59) obtained from the photoelectric detectors 56 and 59 are substantially the same when they receive the scattered light emitted from the foreign particle stuck to the upper surface of the pellicle 1. Then, by comparing the output voltages S(56) and S(59) obtained from the photoelectric detectors 56 and 59 when they receive the scattered light from the foreign particle stuck to the lower surface of the pellicle 1, it is possible to discriminate whether the foreign particle is stuck to the upper surface of the pellicle or the lower surface thereof. For example, if the ratio S(59)/S(56) is more than 2, it can be determined that the foreign particle is stuck to the lower surface of the pellicle, and if not, it can be determined that the foreign particle is stuck to the upper surface of the pellicle.

It should be noted that when polarized light, particularly S-polarization light (light polarized in a direction perpendicular to the incident angle) is used as the illumination light, the discrimination can be more easily and reliably effected. More particularly, when the S-polarization light is supplied to the pellicle under the oblique illumination, the quantity of light reflected on the pellicle will be greater than that in the case where a normal light (not polarized) is supplied to the pellicle under the oblique illumination, with the result that the quantity of light passed through the pellicle and reaching the lower surface thereof will be very little. Consequently, since the quantity of light of the scattered light from the foreign particle stuck to the upper surface of the pellicle remarkably differs from the quantity of light of the scattered light from the foreign particle stuck to the lower surface of the pellicle, by comparing such quantities of light, the discrimination can be effected. For the reasons above, in the above-mentioned embodiments, it is not necessary to use polarized light as to all of the illumination, but polarized light may be used only in the case of the oblique illumination.

As the photoelectric detector, a CCD camera or a camera having an image pickup tube (camera tube) can be used. By treating the photoelectric outputs of the photoelectric detector obtained from the foreign particle by means of the treating means shown in FIG. 6, it is possible to know the sticking condition of the foreign particle.

Further, if the checking operation for discriminating whether the foreign particles are stuck to the upper surface of the pellicle or the lower surface thereof is performed over the whole area of the pellicle, it takes a long time to complete the operation; thus, in order to shorten or reduce the checking time, for example, the following procedures may be adopted; at first, the positions of the foreign particles stuck to the pellicle are previously examined; secondly, said positions are recorded or stored (in an appropriate memory) as co-ordinate values (x,y) in the x-y-z co-ordinate system; then the pellicle is shifted to the position corresponding to each of said co-ordinate values; and the checking operation is performed at the position. In this way, effective checking can be effected.

Further, the foreign particle checking apparatus according to the present invention can be combined with a conventional optical microscope which can effect "epi-dark field illumination". In this case, a light source for illuminating the pellicle laterally at a small incident angle with respect to the pellicle, and the associated lens and filter may be incorporated into the optical microscope. Further, in this case, by repeating the epi-dark field illumination and the oblique illumination alternately and by observing with eye (by means of the microscope) the variation in the quantity of the scattered light from the foreign particle, it is possible to discriminate whether the foreign particle is stuck to the upper surface of the pellicle or the lower surface of the pellicle.

Next, a second embodiment of the checking apparatus according to the present invention will be explained. The checking apparatus in accordance with the second embodiment can automatically detect the presence, size and/or sticking condition of the foreign particle, with the same sensitivity of detection both in the case of the reticle (or mask) with the protection pellicle and in the case of the reticle without the protection pellicle.

Figure 9:
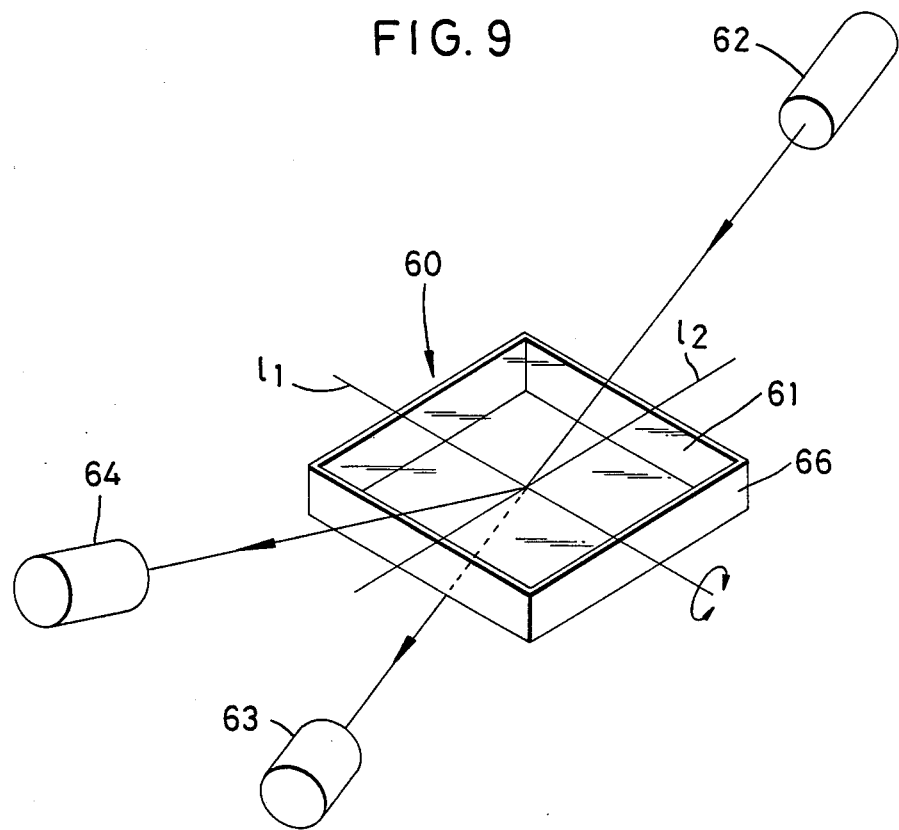
FIG. 9 is a perspective view showing a principle construction of a measuring portion of a checking apparatus according to a second embodiment of the present invention.

As shown in FIG. 9, the checking apparatus includes a measuring portion 60 for measuring permeability of a pellicle 61. A laser beam emitted from a laser source 62 which can output light having a wavelength the same as a laser beam used in the actual surface checking operation is supplied to the surface of the pellicle 61 supported by a supporting frame 66 as the oblique illumination. A photocell or photoelectric detector 63 receives the light passed through the pellicle. By rotating the pellicle by a motor the about a straight line $l_1$ perpendicular to a line $l_2$ formed by projection of the laser beam on the pellicle, and then by measuring the photoelectric voltages of the photoelectric detector 63 as to the incident angles of the laser beam, the relationship between the permeability and the incident angle (feature of variation of the permeability) is measured.

When the pellicle 61 and the supporting frame 66 have already been mounted on the reticle, it is difficult to directly measure the permeability of the pellicle alone. Therefore, in this case, the reflected light is received by a photocell or photoelectric detector 64, the feature of variation of reflection factor is measured from the photoelectric voltages of the detector 63, and the feature of variation of the permeability is presumed on the basis of said feature of variation of the reflection factor.

A range of the rotation of the pellicle about the line $l_1$ is preferably the same as a range of the incident angle between the plane of the pellicle and the incident laser beam (from the laser source 62) or an angular range of the scattered light directed to the photoelectric detector; however, it should be noted that the range of the rotation of the pellicle is not limited to the above, since, as to a light beam having a given wavelength, the feature of variation of reflection factor of said light can be measured within a certain range of the incident angles thereof, and the feature of variation of the permeability thereof can also be fully presumed if the information regarding the also pellicle (that is, the information whether the pellicle is provided with a reflection preventing film coated thereon or not) is obtained.

Further, the wavelength of the measuring laser beam is not necessarily the same as that of the actually checking laser beam, since the permeability of the checking laser beam can be presumed from the permeability of the measuring laser beam. The light from the light source is not necessarily monochromatic light.

Furthermore, although in the present embodiment it is supposed that the pellicle has a uniform thickness all over, if the thickness of the pellicle is not uniform, the non-uniformity or variety of the pellicle can fully be coped with by a method which will be explained later. Preferably, a numerical aperture (N. A.) and a spot size of the measuring laser beam are the same as those of the laser beam of the actual checking apparatus, respectively, but are not so limited.

Figure 10:
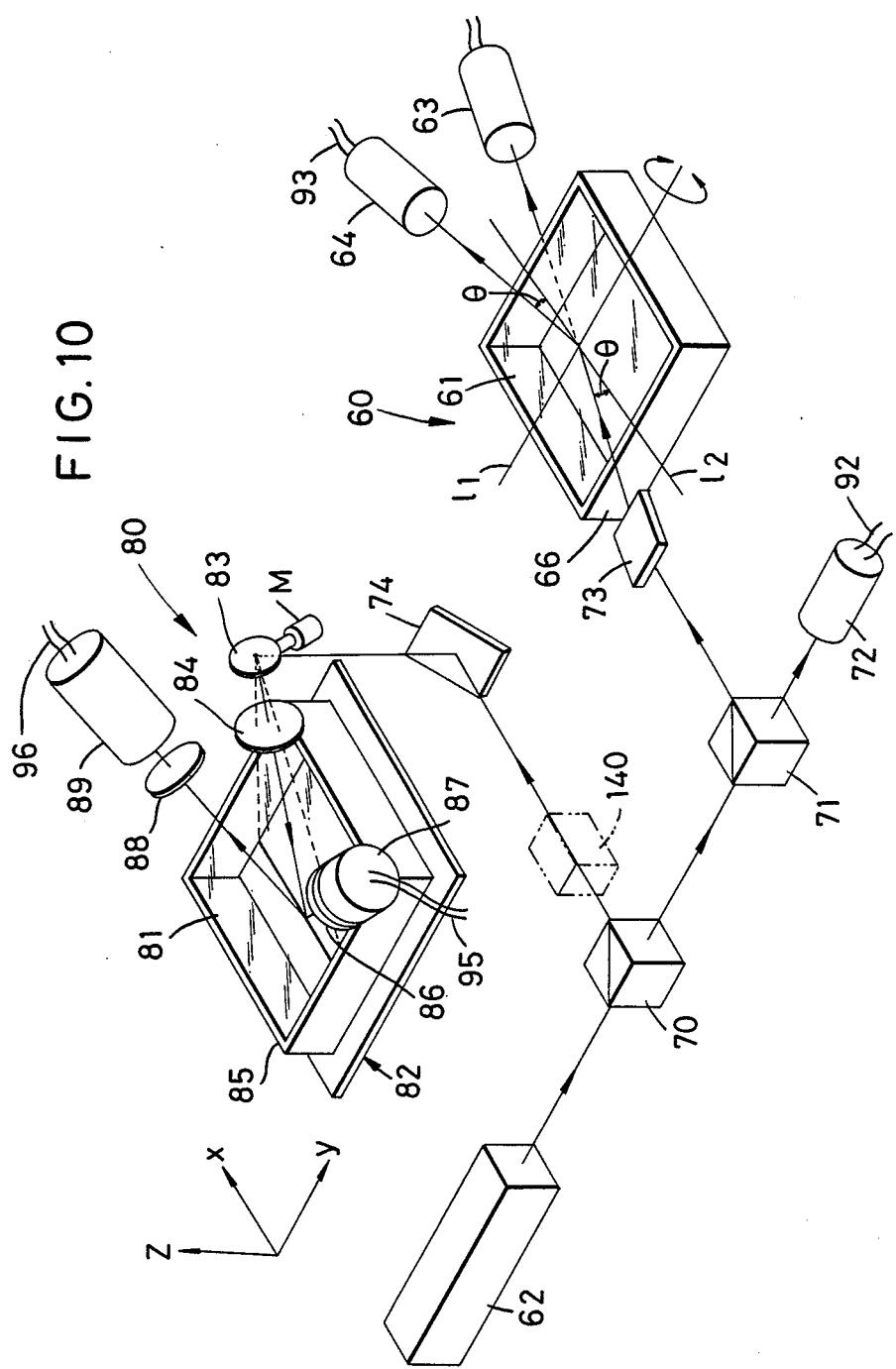
FIG. 10 is a perspective view showing a construction of the checking apparatus according to the second embodiment of the present invention.

FIG. 10 shows a surface checking apparatus into which the measuring portion shown in FIG. 9 is incorporated. The laser beam emitted from the laser source 62 is divided, by a beam splitter 70, into a laser beam directed to the measuring portion 60 and a laser beam directed to a surface checking portion 80. The laser beam directed to the measuring portion 60 is further divided, by a second beam splitter 71, into two laser beams, one of which is received by a photocell 72 for monitoring the quantity of light. The other light beam from the beam splitter 71 is deflected by a mirror 73 and then reaches the pellicle 61 arranged in a predetermined position in the measuring portion 60. The beam passed through the pellicle and the beam reflected on the pellicle are received by photoelectric detectors 63 and 64, respectively. As a function of the incident angle $\theta$ of the beam, by dividing values of the quantity of light received by the photoelectric detectors 63 and 64 by a value of the quantity of light received by the photocell 72, respectively, the feature of variation of permeability of the laser beam and the feature of variation of reflection factor thereof are measured respectively. In this case, for example, when the reflected beam is measured, it is preferable to rotate the photoelectric detector 64 about the axis or line $l_1$, as well as the rotation of the pellicle about said line, in view of reduction or minimization of the light receiver area. It should be understood that, although not shown in the drawings, an appropriate optical system (lenses and the like) is associated with or provided in the measuring portion 60.

After the feature of variation of the permeability regarding the pellicle/incident-angle is measured by the measuring portion 60, the pellicle itself or the reticle provided with the pellicle is conveyed into the surface checking portion 80 by means of an appropriate conveying device (not shown). In the illustrated embodiment, a reticle 82 provided with the pellicle is checked. In the surface checking portion 80, the laser beam from the beam splitter 70 is deflected by a mirror 74 and then is reflected by a scanner mirror 83 which can be rocked by means of a motor M to undergo a so-called "laser beam deflection". The scanning laser beam from the scanner mirror 83 is focused on a locus to be scanned on the surface of the reticle 82 by means of an objective lens 84 and a beam expander optical system (not shown). The scattered light from the foreign particle stuck or adhered to the reticle surface is received by photoelectric detectors 87 and 89 through lenses 86 and 88, respectively.

Here, since the laser beam is sent to the pellicle as the oblique illumination, the permeability of the pellicle regarding the laser beam is smaller than that in the epi-illumination. Further, when the optical supplying system (the objective lens 84 and the like) is not a so-called "telecentric optical system", the permeability of the pellicle varies in response to a variation of the incident angle. Furthermore, since an angle between the plane of the pellicle and the beam of the scattered light directed to the light receiver optical system (lenses 86, 88) varies in dependence upon the scanning position of the laser beam, for example, the quantity of light received by the photoelectric detectors 87 and 89 and emitted from the foreign particle on the reticle 82 with the pellicle differs from that in the case of the reticle without the pellicle, even if the laser beam is on the same scanning position.

Similarly, the quantity of light of the scattered light from the foreign particle stuck to the lower surface of the pellicle 81, also varies in dependence upon the scanning position of the laser beam. In this case, the variation of the quantity of light can be presumed on the basis of the thickness of the pellicle and the like. Since this information can be obtained by the measuring portion 60, such variation can be easily corrected upon detection of the foreign particle. Such correction of the variation is not necessarily effected upon detection of the foreign particle. For example, the correction can be performed by an operation in software, upon displaying the size and/or position of the foreign particle as a checked result after the detection of the foreign particle. In this case, the feature of variation of the permeability and/or the feature of variation of the reflection factor can be measured after the checking of the foreign particle. Further, when the surface of the pellicle 81 is checked by means of this apparatus, the locus to be scanned by the spot light of the laser beam is shifted onto the pellicle by lowering the reticle 82 by means of the stage (not shown) capable of moving in Z-direction.

Figure 11:
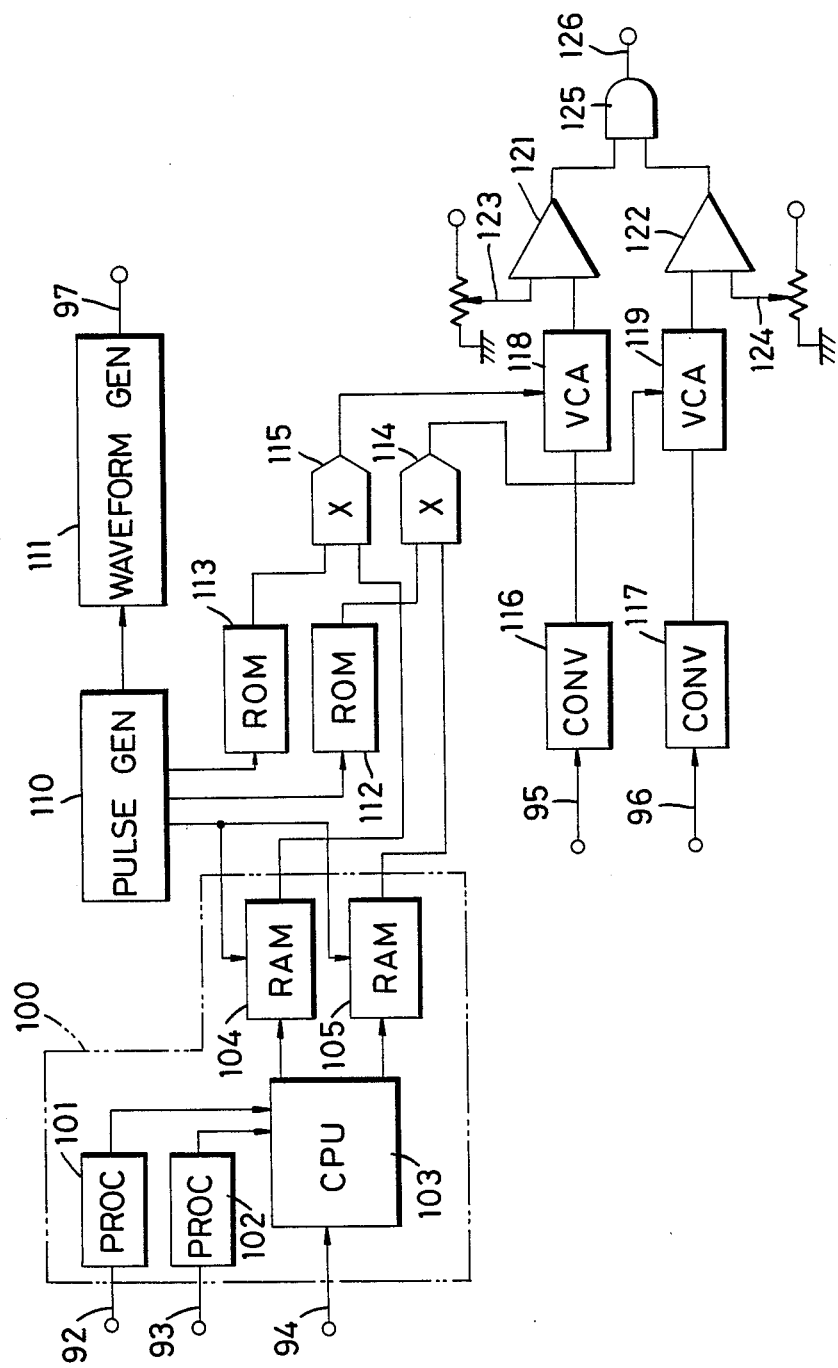
FIG. 11 is a circuit block diagram showing a construction of a signal treatment circuit.

FIG. 11 shows a block diagram for treating the photoelectric signals generated in the apparatus of FIG. 10. A photoelectric signal 92 from the photocell 72 is inputted to a CPU 103 through a pre-treatment circuit 101 including a voltage transducer, an A/D converter and the like. A photoelectric signal 93 from the photoelectric detector 64 for receiving the reflected light in the measuring portion 60 is also inputted to the CPU 103 through a pre-treatment circuit 102 including a voltage transducer, an A/D converter and the like. At the same time, a data signal 94 which represents an angle converted from the rotation of the pellicle 61 about the line l is also inputted to the CPU 103 through a rotary encoder (not shown). After these data signals are inputted to the CPU 103 sufficient to obtain the feature of variation of the permeability of the pellicle regarding the incident angle for the desired angular range, the CPU 103 creates or forms a table representing the relationship between the permeability and the incident angle of the laser beam (that is, the feature of variation of the permeability). Further, the CPU 103 finds out by an operation the permeability in response to the variation of the scanning position of the laser beam in the x-direction, and sends the found data to a RAM 104 and a RAM 105. The RAM 104 stores the data regarding the signal from the photoelectric detector 87, whereas the RAM 105 stores the data regarding the signal from the photoelectric detector 89. Therefore, when a value obtained by counting time-series pulses from a pulse generator 110 is applied to the RAM 104 and RAM 105 as an address, the permeability at that scanning position can be automatically read out.

The pre-treatment circuits 101, 102, CPU 103, RAM 104 and RAM 105 constitute an inputting means, whereas a correcting means is constituted by multipliers 114 and 115, and voltage controlled amplifiers 118 and 119. Since the Pre-treatment circuits 101, 102, CPU 103, RAM 104 ad RAM 105 form a portion for holding the information regarding the pellicle, said portion is referred to as "pellicle information holding portion 100".

The scattered light from the foreign particle is received by the photoelectric detectors 87 and 89 by which photoelectric signals 95 and 96 corresponding to the quantities of light of the received light beams are generated. These signals 95 and 96 are converted to voltages by means of voltage transducers 116 and 117, respectively. A waveform generator 111 creates, in synchronism with the output pulses of the pulse generator 110, a saw tooth wave 97 which is sent to a driving circuit for the scanner mirror 83. Therefore, by counting the time-series pulses from the pulse generator 110, it is possible to know the scanning position of the laser beam in the x-direction. Thus, it is also possible to determine the scanning position in the x-direction when scattered light is being emitted, on the basis of the counted value.

When the reticle without the pellicle is checked, since the quantity of light of the scattered light received by the photoelectric detectors 87 and 89 varies in response to the variation of light receiving angles thereof depending upon their positions in the x-direction, the above-mentioned voltage controlled amplifiers 118 and 119 are provided for adjusting gains with respect to each of signals from the voltage transducers 116 and 117 to standardize the quantity of light. An amplification degree conversion constant for this purpose is previously found out by experiments and the like and is stored in ROMS 113 and 112. Thus, amplification degree conversion values can be sequentially read out from the ROMs 113, 112 in response to the time-series pulses from the pulse generator 110 and can be inputted to the voltage controlled amplifiers 118 and 119 through the multipliers 115 and 114, thereby effecting the correction of the photoelectric signals regarding the quantity of the scattered light in accordance with the scanning position in the x-direction. The other input constant of each of the multipliers 115 and 114 is set or selected to "1" when the reticle without the pellicle is checked; in this case, values from the ROMs 113 and 112 are inputted to the voltage controlled amplifiers 118 and 119 just as they are. When the reticle provided with the pellicle 81 is checked, the corrected values regarding the scanning positions in the x-direction should be further corrected or amended.

More particularly, if the position of the foreign particle in the x-direction is obtained, it is possible to determine the incident angle of the laser beam directed to the foreign particle. Further, the incident angles (with respect to the pellicle 81) of the light beams (among the scattered light from the foreign particle) directed to the photoelectric detectors 87 and 89 can also be easily found out by the geometrical positions of these photoelectric detectors. Thus, by inputting the time-series pulses from the pulse generator 110 corresponding to the positions of the light spot in the x-direction on the scanning locus to the RAM 105 and RAM 104 which store the data regarding the feature of variation of the permeability (or the reflection factor) as the table representing the permeability (or reflection factor) with respect to the scanning positions, the correction values for the permeable amount of the scattered light in accordance with the scanning positions of the laser beam in the x-direction can be sequentially obtained. In this way, since the correction values corresponding to the variation of the scanning positions of the laser beam (light spot) in the x-direction due to the existence of the pellicle are similar to the correction values stored in the ROMs 113 and 112, by multiplying both of the correction values by means of the multipliers 114 and 115, and then by inputting the result of multiplication to the voltage controlled amplifiers 118 and 119 as the amplification degree conversion value in case of the checking of the reticle having the pellicle, it is possible to duly standardize the quantity of the scattered light, even if the pellicle exists. Each of the so standardized signals from the voltage controlled amplifiers 118 and 119 is compared, by comparators 121 and 122, with each of reference voltages (slice level) 123 and 124, respectively, thereby creating a binary mode with respect to the quantity of the scattered light having a level larger than a predetermined signal level. Thus, when both of the quantities of the scattered light are larger than said predetermined level, an AND circuit 125 outputs a digital signal 126.

Since the scattered light emitted from the foreign particle is deflective, when data regarding a variation in the detection due to the deflected components of the scattered light and the like have previously been inputted to the CPU as various physical conditions, it is apparent that the correction will be more accurate.

It should be understood that the correction means is not limited to the illustrated one; for example, the correction method can be performed by varying the reference voltages 123 and 124 on the basis of the information from the pellicle information holding portion 100, or by varying a displaying level when the information regarding the size and position of the foreign particle are displayed on a CRT after the permeability is measured in the measuring portion 60 and the foreign particle is detected. As such displaying method, for example, a method described in the literature "PROCEEDINGS OF SPIE" (Vol. 470, published on March 14th and 15th, 1984) can be adopted. In this case, an operation in the software corresponds to the correction method. Further, it is apparent that, if the feature of variation of the permeability of the pellicle has already been known, the measuring portion 60 may not be used, and thus the data regarding the permeability of the pellicle can be inputted to the CPU before the checking operation is initiated.

Figure 12A:
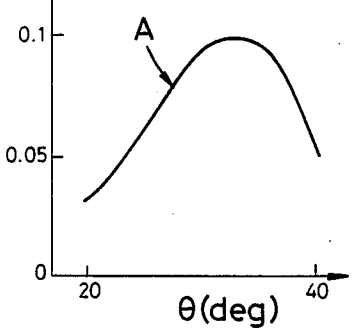
FIGS. 12A and 12B are graphs showing variation features of reflectivity.
Figure 12B:
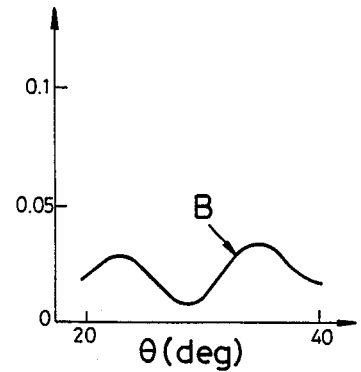
Figure 12C:
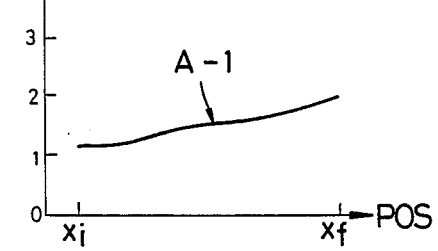
Figure 12D:
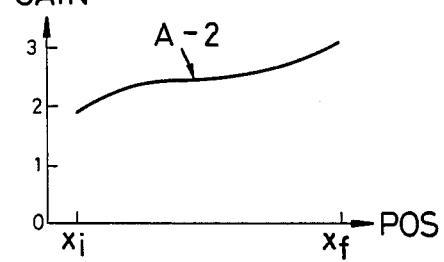
Figure 12E:
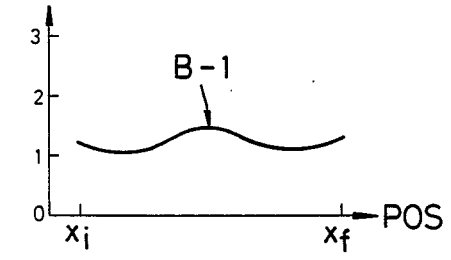
Figure 12F:
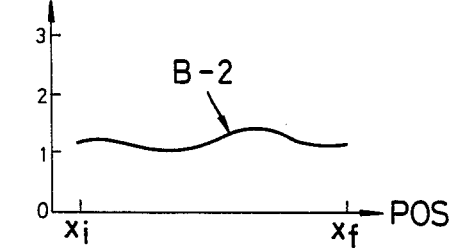

Furthermore, when the data regarding the permeability inputted to the CPU are outputted to the RAMs 105 and 104, it is possible to use a method in which some of estimated data have previously been inputted to the CPU, then the data most nearly allied to data obtained by the measuring portion 60 are picked up among the inputted data, then the picked-up data are converted to the permeability corresponding to the scanning position (as correction factors), and lastly the correction factors are inputted to the RAMs 105 and 104. In this case, the data stored in the CPU and RAMs are provided or determined, for example, as ones shown in FIGS. 12A–12F. Some of the data regarding the feature of variation of the reflection factor (in dependence upon the incident angle) determined by the kind of the pellicles are stored in the CPU. Here, it is assumed that two data regarding the feature of variation of the reflection factor as representatively shown in FIGS. 12A and 12B are being stored in the CPU as the data base. In FIGS. 12A and 12B, the abscissa (horizontal axis) represents angle $\theta$ (deg.) between the plane of the pellicle and the incident light beam, and the ordinate (vertical axis) represents the reflection factor. If it is judged, in the CPU, that the feature of variation of the reflection factor of the scattered light (received by the photoelectric detector 64) within the angle between 20° and 40° measured by the measuring portion 60 is most nearly allied to the feature A shown in FIG. 12A, the CPU outputs the data corresponding to correction curves A-1 and A-2 shown in FIGS. 12C and 12D to the RAMs 104 and 105, respectively. In FIGS. 12C and 12D, the abscissa represents the position of the light spot of the laser beam on the scanning locus, and the ordinate represents the amount of gain adjustment applied to the multipliers 115 and 114. In FIG. 12C, the gain determined by the correction curve A-1 is given, for example, with respect to the photoelectric signal 95 from the photoelectric detector 87; in the position $x_i$ where the checking operation is initiated, the correction is not effected (GAIN=1), whereas in the position $x_f$ where the checking operation is completed, the correction is so effected that the amplification degree is substantially twice larger than that in the initial position (GAIN=2). On the other hand, in FIG. 12D the gain determined by the correction curve A-2 is given with respect to the photoelectric signal 96 from the photoelectric detector 89; the correction is continuously effected so that the gain increases to about 2 in the initial position $x_i$ and about 3 in the position $x_f$ where the checking operation is completed. Further, when the CPU judges that the feature of variation of the reflection factor actually measured is nearly allied to the feature B shown in FIG. 12B, the CPU outputs the data regarding the correction curves B-1 and B-2 shown in FIGS. 12E and 12F to the RAMs 104 and 105, respectively.

It should be understood that more delicate corrections can be performed regardless of the quality and size of the pellicle, if the above data base regarding the feature of variation of the reflection factor (or permeability) or the gain correction curves (or features) are previously prepared in more details with respect to many kinds of features.

Figure 13:
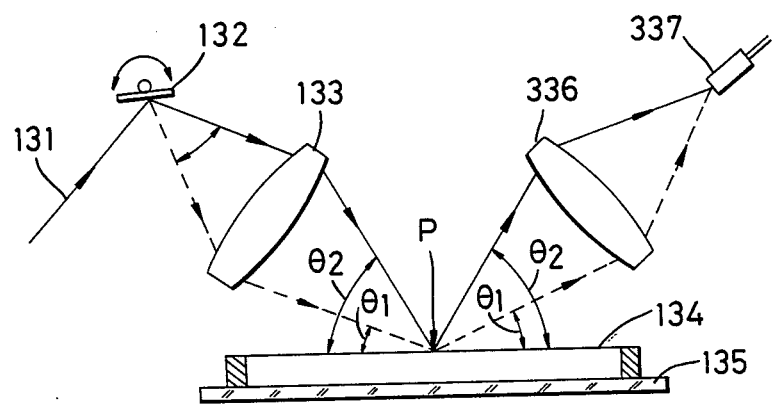
FIG. 13 is a perspective view showing a modification of the measuring portion.

FIG. 13 shows another embodiment of a measuring means for measuring the feature of variation of the permeability (the relationship between the permeability and the incident angle) of the pellicle, which corresponds to the measuring portion 60 of FIG. 10. In the measuring means shown in FIG. 13, it is assumed that the reflection factor of the pellicle is measured. A laser beam 131 reaches a scanner mirror 132 which can be rotatably vibrated in the directions shown by an arrow, where the laser beam is deflected. The deflected laser beam is refracted by a condenser lens 133 to focus at a point P on the pellicle 134 covering a reticle 135.

Consequently, an angle between the plane of the pellicle and the incident laser beam at the point P varies between $\theta_1$ and $\theta_2$, and an angle between the plane of the pellicle and the regularly reflected beam also varies between $\theta_1$ and $\theta_2$. The regularly reflected light beam is received by a photoelectric detector 337 through a condenser lens 336. Since an angle of the rotational vibration of the scanner mirror 132 is related to the incident angle of the incident laser beam on the pellicle, the feature of variation of the permeability (or reflection factor) of the pellicle 134 can be presumed on the basis of the rotational angle of the scanner mirror and the photoelectric signal from the photoelectric detector 337. This embodiment has an advantage that the feature of variation of the permeability can be measured without rotation of a supporting frame for the pellicle and/or without movement of the photoelectric detector.

In this embodiment, too, the permeability may vary due to a thickness of the pellicle itself; thus, it is preferable to measure the permeability of the pellicle at different positions obtained by shifting the pellicle horizontally along the line $l_1$ or $l_2$ shown in FIG. 10. In this case, if thee is a difference in thickness in the scanning direction of the laser beam in the surface checking portion 80 (FIG. 10), the correction may be effected by the aforementioned voltage controlled amplifiers 118 and 119 by inputting data regarding such difference to the CPU 103 in the same manner as mentioned above. Further, if there is a difference in thickness in the y-direction perpendicular to the scanning direction, the gains of the voltage controlled amplifiers 118 and 119 may be adjusted in synchronism with the movement (per unit) of the reticle in the y-direction.

Furthermore, in the surface checking portion 80, the laser beam may be supplied from the reticle side (i.e., underside of the checking portion 80) and the scattered light received at the pellicle side (i.e., upper side of the checking portion). Such construction can also be adopted in the case where the reticle is covered on its both sides by the pellicles.

Further, the surface checking portion 80 shown in FIG. 10 can be constructed integrally with the measuring portion 60. In this case, by constructing the scanner mirror 83 so that it permits temporary stopping of the light spot at the center of the scanning locus and by arranging the photoelectric detector 64 so that it can receive the regularly reflected light, the feature of variation of the permeability of the pellicle can be measured as well. In the measuring portion 60, it is not necessary to vary the incident angle of the laser beam on the pellicle continuously; by measuring the permeability of the pellicle with respect to at least two incident angles, it is possible to obtain the permeability with respect to other incident angles by an operation on the basis of the measured data.

In the above-mentioned second embodiment, the checking operation regarding the reticle having the protection pellicle positioned spaced apart from the reticle surface has been explained; however, the checking operation can be adapted to the checking of the reticle having a protection glass plate affixed to a reticle surface on which a pattern such as a chrome pattern is formed, as well.

Furthermore, in the above-mentioned embodiments, the sensitivity of the detection was effected after the photoelectric detectors received the scattered light; however, the sensitivity of the detection can be effected, for example, by providing an adjuster for adjusting the quantity of light (i.e., an attenuator) 140 such as an AOM (acoustic optical modulator) in a path of the laser beam between the beam splitter or half-prism 70 and the mirror 74 and by quickly adjusting the light intensity of the laser beam scanning the reticle surface (or the pellicle surface) by an amount determined according to the scanning position.

It is difficult to completely correct the variation of the sensitivity as to the measurement of the feature of variation of the permeability by merely adjusting the light intensity of the laser light spot, when the laser beam is supplied to the reticle surface in the oblique illumination and a plurality of the photoelectric detectors are directed to the scanning locus on the reticle surface at different spaced positions. However, by modulating the intensity of the light spot in accordance with the scanning positions, it is possible to remarkably decrease or reduce the amount of correction regarding the electrical system as to the photoelectric detectors, with the result that a comprehensive dynamic range regarding the detection of the foreign particle can be enlarged. This means that the foreign particles having various sizes can be checked with proper sensitivity. Even when the laser beam is supplied as the oblique illumination, the correction can be fully effected by merely modulating the intensity of the light spot according to the position of the photoelectric detectors.

Next, a third embodiment of the present invention will be explained. The checking apparatus according to the third embodiment enables the checking of the surface of the reticle without being obstructed by the supporting frame for the pellicle.

Figure 14:
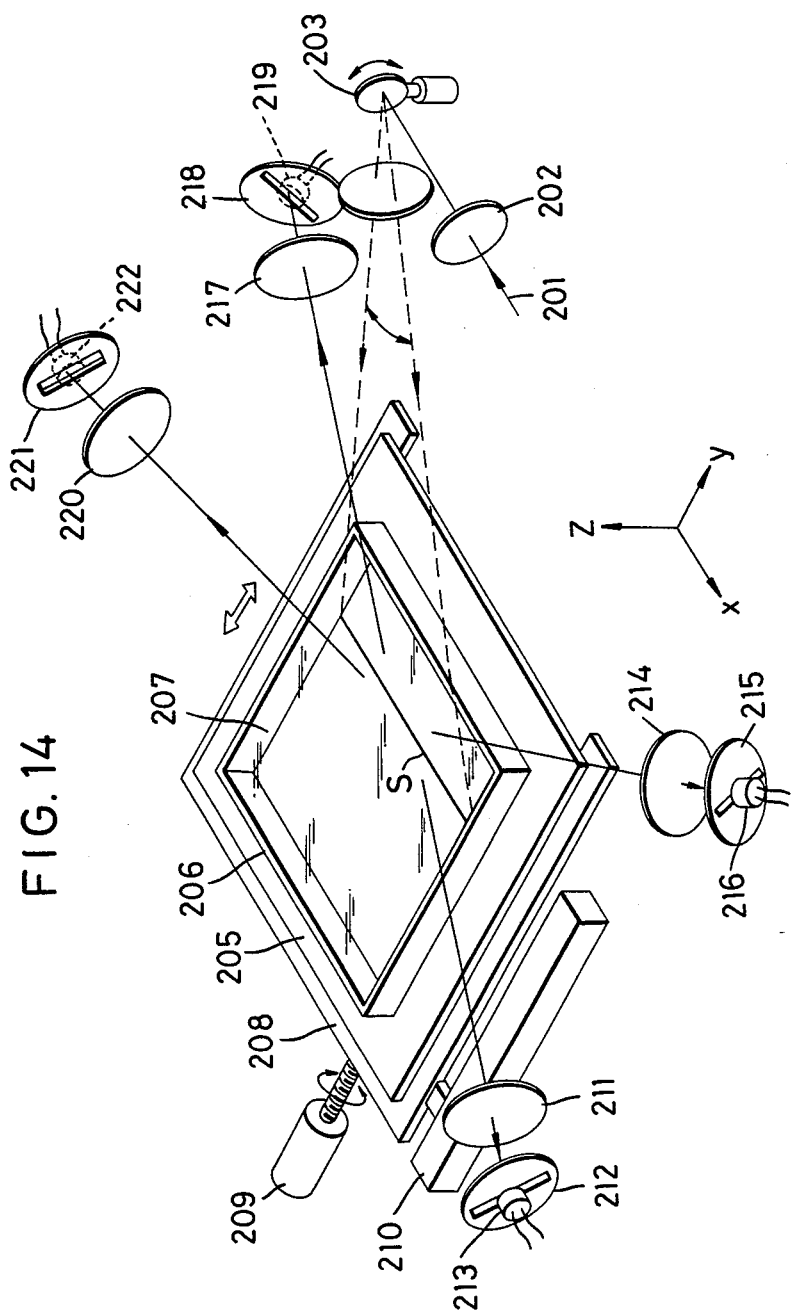
FIG. 14 is a perspective view showing a checking apparatus according to a third embodiment of the present invention.

In FIG. 14, a stage 208 for shifting a reticle 205 can be driven in the y-direction by means of a motor 209, a lead screw and the like. An amount of movement of the stage 208 is measured by a length meter (device for measuring the length) 210 such as a linear encoder. A pellicle 207 is mounted on the reticle 205 through a supporting frame 206 for supporting the pellicle. An incident angle of a laser beam 201 onto the reticle is selected in a range of 80°–10° so that the incident laser beam is not obstructed or interrupted by the supporting frame 206. The laser beam 201 can scan the reticle in the x-direction with the aid of a scanner mirror 203. In this case, the laser beam may be polarized by a deflector 202 so that the incident beam is perpendicular to the plane of the reticle (i.e., x-y plane in FIG. 14) (S-polarization). In order to scan the whole area of the reticle by the laser beam, the scanner mirror 203 is vibrated and, at the same time, the stage 208 is moved in the y-direction by means of the motor 209 at a speed lower than the scanning speed of the laser beam. The length meter 210 outputs a measured result corresponding to the illuminating position (scanning position) in the y-direction. With respect to the x-direction, the illuminating position is measured by a signal representing the rotational angle of the scanner mirror 203. In order to detect the scattered light from the foreign particle stuck on the reticle, photoelectric detectors 213 and 222 are arranged in a plane which is perpendicular to the reticle plane and which includes a scanning line or locus S and photoelectric detectors 216 and 219 are arranged in a plane positioned on the same side as the mirror 203 with respect to the first-mentioned plane. In front of the photoelectric detectors 213, 216, 219 and 222, condenser lenses 211, 214, 217 and 220 are arranged. During the movement of the reticle in the y-direction, when the scanning beam approaches the pellicle supporting frame 206, the reflected light from the upper and lower surfaces of the reticle illuminates the supporting frame, which would generate stray light. Slit plates 212, 215, 218 and 221 are provided for preventing such stray light from the supporting frame from entering into the corresponding photoelectric detectors 213, 216, 219 and 222. These slit plates are arranged in positions conjugated with the scanning line S on the reticle with respect to the corresponding condenser lenses 211, 214, 217 and 220. Each of the photoelectric detectors is arranged in contact with or close to the corresponding slit plate so that the detector is situated immediately behind a slit of the corresponding slit plate. Alternatively, a relay optical system (not shown) may be provided between each of the slit plates and the corresponding photoelectric detector to achieve the same effect as the above. It is more advantageous that the slit has a wedge-shape having a wider upper end rather than an elongated rectangular shape, since, in the light receiving system for receiving the light from the oblique direction, as the scanning position varies, the width of the slit also varies in accordance with a transversal multiplying factor of the corresponding condenser lens.

Figure 15:
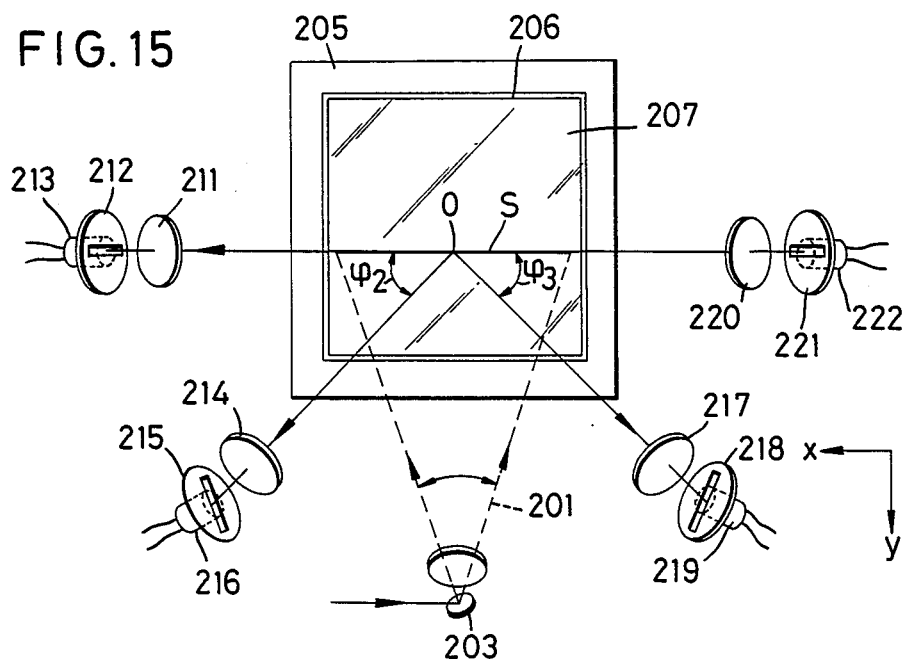
FIG. 15 is a plan view of the checking apparatus of FIG. 14.
Figure 16:
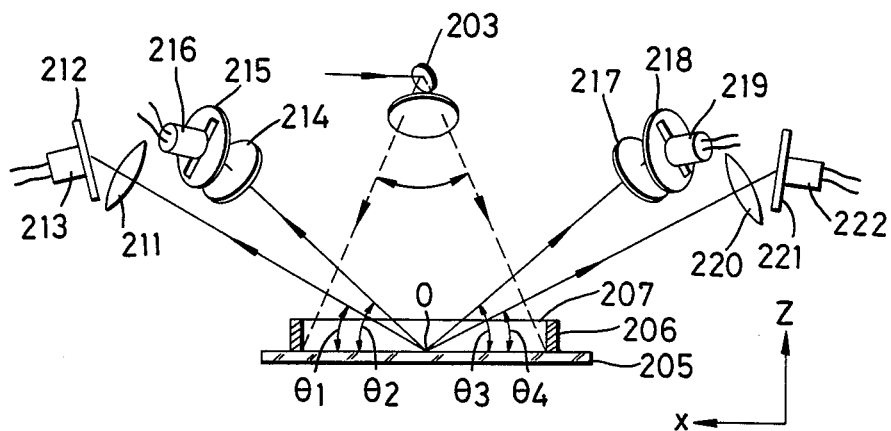
FIG. 16 is a side view of the checking apparatus of FIG. 14.

FIG. 15 is a plan view of the apparatus of FIG. 14, and FIG. 16 is a side view of the apparatus of FIG. 14 looked at from the right (FIG. 14) in the y-direction. In FIG. 15, the photoelectric detectors 213 and 222 are arranged in the plane which includes the scanning line S and which is normal to the plane of the reticle, and the photoelectric detectors 216 and 219 are so arranged that azimuths $\phi_2$ and $\phi_3$ thereof are in the order of 15°-80°, respectively. Further, as shown in FIG. 16, the four photoelectric detectors 213, 216, 219 and 222 are arranged in such a manner that angles $\theta_1$, $\theta_2$, $\theta_3$ and $\theta_4$ between the plane of the reticle and the optical axes of the corresponding condenser lenses 211, 214, 217 and 220 are in the order of 10°-80°, respectively on the illumination side (i.e., above the reticle) and that they are symmetrical with each other in regard to a plane which includes the incident light beam reaching a center 0 of the scanning locus S and that they are included in planes including the reflected light beams from the point 0. Further, the condenser lenses 211, 214, 217 and 220 are arranged substantially equidistant from the center 0 of the scanning locus and are positioned so that the optical axes of these lenses cross the scanning line S (In the illustrated embodiment these optical axes cross each other on the center 0 of the scanning locus S).

Next, the detecting operation for detecting the foreign particle stuck to the reticle will be explained.

During the scanning of the reticle 205 by the laser beam, when the laser beam illuminates an edge of a pattern regularly formed on the reticle, the scattered light is strongly oriented to some directions. Thus, in this case, one of the four photoelectric detectors outputs a remarkably strong output signal. On the other hand, when the laser beam illuminates the foreign particle, the scattered light from the foreign particle is dispersed over all the directions; thus, the four photoelectric detectors output photoelectric signals equal to or substantially the same as each other. A circuit for detecting the foreign particle from these photoelectric signals will be explained below.

Figure 17:
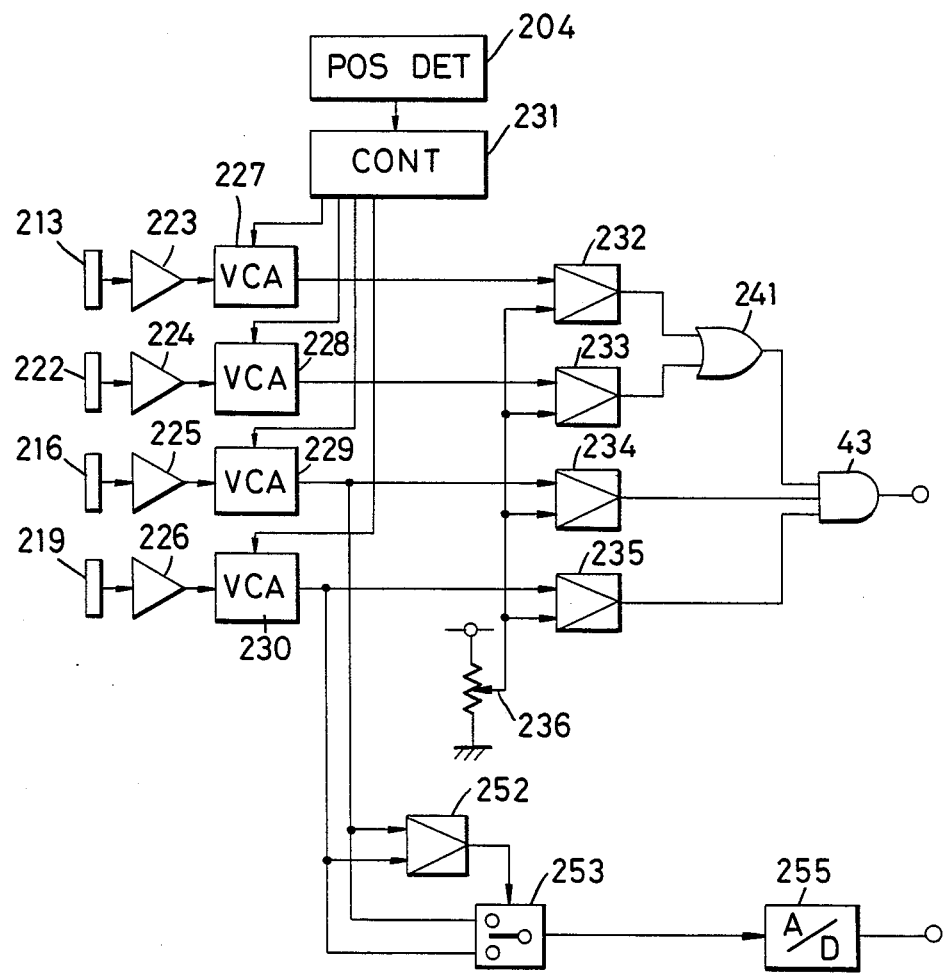
FIG. 17 shows a signal treatment circuit.

As shown in FIG. 17, the outputs of the four photoelectric detectors 213, 216, 219 and 222 are amplified by means of amplifiers 223, 224, 225 and 226, respectively. However, the output levels of the four photoelectric detectors are influenced by the position of the foreign particle on the reticle. More specifically, the output level of the detector positioned near the foreign particle is larger than that of the detector positioned remotely from the foreign particle. Thus, it is necessary to correct each of the output levels in accordance with the position of the foreign particle.

To this end, amplification degree converters such as voltage controlled amplifiers 227, 228, 229 and 230 where the amplification degree is varied by the applied voltage are directly connected to the amplifiers 223, 224, 225 and 226, respectively to adjust the amplification degrees by means of a controller 231. A position detector 204 outputs a signal corresponding to the rotational position of the scanner mirror 203. The controller 231 receives the signal from the detector 204 and outputs, on the basis of previously stored values, voltages which are inputted to corresponding VCAs in accordance with the scanning positions of the laser beam. The amplification degrees of the VCAs 227, 228, 229 and 230 are determined in accordance with the positions of the detectors 213, 216, 219 and 222. By performing the correction in this way, it is possible to obtain outputs depending only upon the size of the foreign particle, regardless of the position of the foreign particle.

Thereafter, these outputs are compared with a reference level 236 by means of comparators 232, 233, 234 and 235, respectively, thereby being converted to a binary mode. This reference level 236 is not necessarily constant all the time, but may be varied in synchronism with the rotational vibration of the scanner mirror. Further, different reference levels may be inputted to the corresponding comparators. After the outputs from the detectors 213 and 222 situated on an extension of the scanning line S are compared with the reference level, when at least one of the compared results has an H level, an OR circuit 241 outputs the H level. When the laser beam is scanning an area of the reticle near the supporting frame 206, one of the to detectors 213 and 222 cannot receive the scattered light from the foreign particle, since the scattered light is interrupted by the supporting frame. However, if only the foreign particle exists on the scanning line, since at least one of the detectors 213 and 222 surely receives the scattered light from the foreign particle, the OR circuit outputs the H level representing the "presence" of the foreign particle. The output from the OR circuit 241 and the outputs from the two remaining comparators 234 and 235 are inputted to an AND circuit 243. The AND circuit 243 outputs a foreign particle detecting signal only when the laser beam illuminates the foreign particle on the reticle. In order to obtain a rough size of the foreign particle without the influence of the scattered signals from the pattern formed on the reticle, it is effective to compare the intensity of the smaller signal among the photoelectric signals from the detectors 216 and 219 with prearranged data regarding the relationship between the size of the foreign particle and the intensity of signal. Such method is disclosed in U.S. Pat. No. 4,610,541. In the present embodiment, such method can be adopted.

More particularly, the outputs from the VCAs 229 and 230 are inputted to a comparator 252 and a switching device 253. The comparator 252 actuates the switching device 253 in such a manner that among the outputs from the VCAs 229 and 230 the smaller one is selected. The selected smaller analogue signal is inputted to an A/D converter 255 to be converted into a digital signal. By comparing the output signal from the A/D converter 255 with statistically prearranged data representing the relationship between the size of the foreign particle and the input signal, by means of a computer (not shown), it is possible to know a rough size of the foreign particle.

Next, a fourth embodiment of the present invention will be explained. The fourth embodiment enables checking the foreign particle with sensitivity of detection (i.e., diameter of the scanning beam) according to the allowance as to the size of the foreign particle and at a speed corresponding to said beam diameter, by changing the beam diameter on the reticle in response to the foreign particle.

Figure 18:
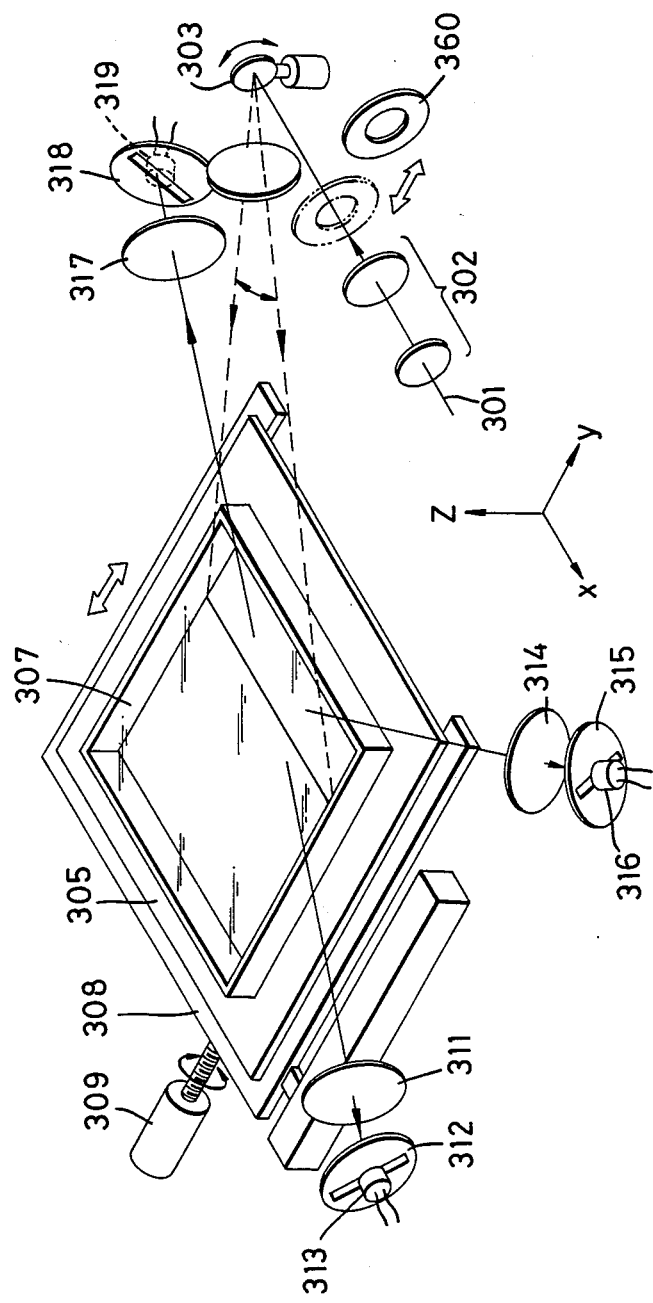
FIG. 18 is a perspective view showing a checking apparatus according to a fourth embodiment of the present invention.

In FIG. 18, a table or stage 308 for supporting a reticle 305 provided with a pellicle 307 can be shifted in the y-direction by means of a motor 309 (as in the case of FIG. 14) and can also be shifted in the z-direction by a driving means (not shown).

A laser beam 301 is adjusted to have any beam diameter by an expander 302 and the like and then is supplied to the reticle or the pellicle through a scanning mirror 303. Three sets of detecting assemblies 311-313, 314-316 and 317-319 are arranged in spaced positions in the same manner as the detecting assemblies 211-213, 214-216 and 217-219 of FIG. 14. An aperture member 360 can be inserted in a path of the laser beam between the expander 302 and the scanner mirror 303. When the aperture member 360 is inserted in the above-mentioned path, a numerical aperture of the optical system for the incident laser beam decreases. Consequently, the beam diameter of the laser beam on a focused point (i.e., on the reticle or on the pellicle) increases. Since a scanning width in the y-direction which is scanned by a single scanning operation performed by the laser beam moving in the x-direction can be enlarged in accordance with the increase of the beam diameter, when the beam diameter is increased, the speed of movement of the stage 308 can be faster.

Therefore, when a pellicle having a great allowance as to the size of the foreign particle stuck thereto is checked, it is preferable to enlarge the beam diameter of the scanning laser beam and to increase the speed of movement of the stage, thereby considerably shortening the scanning time for scanning the whole area of the pellicle, in comparison with the scanning time by means of the laser beam having a normal beam diameter.

Figure 19:
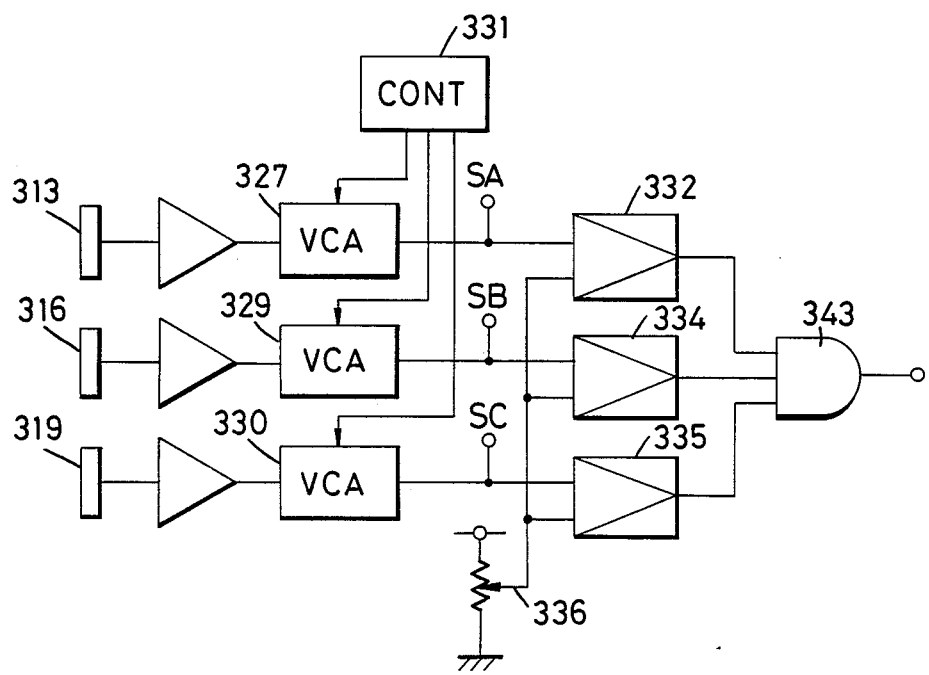
FIG. 19 is a circuit showing means for treating photoelectric outputs.

In FIG. 19, since each of the outputs from the photoelectric detectors 313, 316 and 319 varies in accordance with a distance between the laser spot and each detector, these outputs are corrected in accordance with the position of the foreign particle on the basis of prearranged data by means of voltage controlled amplifiers 327, 329 and 330 under the control of a controller 331, as in the case of FIG. 17. The corrected outputs are compared with a reference level 336 by means of comparators 332, 334 and 335, respectively; when the output of the comparator has H level, a detecting signal is generated in an AND circuit 343. The size of the foreign particle is determined by utilizing each output SA, SB, SC from each of the VCAs (voltage controlled amplifiers) 327, 329 and 330. More particularly, at first, the relationship between the size of the foreign particle and the signal level of the smallest output among the outputs SA, SB and SC is statistically prepared previously; then, by comparing the data regarding said relationship with an actually obtained output signal, a rough size of the foreign particle can be obtained.

Figure 20:
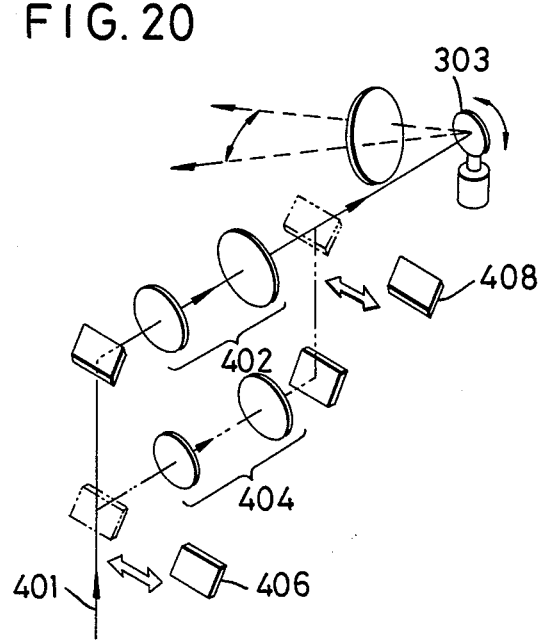
FIG. 20 is a perspective view showing a modification of the fourth embodiment of the present invention.
Figure 21:
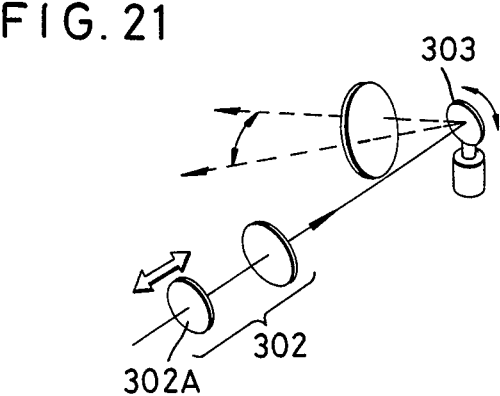
FIG. 21 is a perspective view showing another modification of the fourth embodiment of the present invention.

When the aperture member 360 is used for increasing the beam diameter, since the numerical aperture decreases and the quantity of light of the laser beam also decreases, it is desirable to adjust the comparison system by uniformly changing the amplification degrees of the VCAs 327, 329 and 330 by means of the controller 331, or by changing the reference voltage 336. With this adjustment, even when the beam diameter is changed, the sensitivity of detection (determination of the size of the foreign particle and the like) regarding the foreign particle is maintained in an optimum condition in accordance with the beam diameter. In place of the aperture member 360, two expanders 402 and 404 having different multiplying factors and change-over mirrors 406 and 408 for changing over paths of a laser beam 401 (FIG. 20) may be provided for changing the beam diameter of the laser beam. When the change-over mirrors 406 and 408 are out of the path of the laser beam, the laser beam 401 is enlarged by an expander 402 and then is sent to the scanner mirror 303. When the change-over mirrors 406 and 408 are inserted in the light path of the laser beam simultaneously, the laser beam 401 is enlarged or expanded by a second expander 404 and then is sent to the scanner mirror 303. As a modification of the above construction, for example, an expander having a variable multiplying factor and comprising a zoom system may be used in place of the expanders 402 and 404. Further, as shown in FIG. 21, a focus of the incident laser beam illuminating the reticle may be slid or shifted, thereby changing the beam diameter of the incident laser beam. When the foreign particle stuck to the pellicle is checked, the beam diameter of the laser spot on the pellicle is changed by shifting one of lenses (for example, a lens 302A) of the expander 302 on the light path without altering the position of the stage 308 in the z-direction, thereby altering the focus position of the laser beam.

The checking position where the reticle is checked differs from the checking position where the pellicle is checked due to the presence of the supporting frame. Therefore, it is necessary to determine or select the widths of the slits of the slit plates 312, 315 and 318 so that the scattered light is not interrupted by the slit plates.

Of course, it is possible to change the beam diameter of the laser spot on the pellicle by shifting the stage 308 in the z-direction without altering the focus position of the laser beam (that is, without shifting the lenses of the expander 302).

What is claimed is:

1. An apparatus for detecting foreign particles on a surface of a substrate, comprising:
   a supplying means for supplying a light beam which forms a light spot repeatedly shifting along a scanning line on the surface of said substrate, to the surface of said substrate from an oblique direction;
   a shifting means for shifting said substrate to vary a position of said scanning line;
   first and second light detectors arranged in a first plane which includes said scanning line and is perpendicular to the surface of said substrate and positioned symmetrically with respect to an incident plane of said light beam passing through a center of said scanning line, said first and second light detectors generating photoelectric outputs, respectively;
   third and fourth light detectors arranged in a second plane parallel to said first plane and positioned symmetrically with respect to said incident plane, said third and fourth light detectors generating photoelectric outputs, respectively;
   an operating means for receiving the photoelectric outputs of said first and second light detectors and for generating an output signal representing a logic sum of said photoelectric outputs; and
   a discriminating means for receiving the output signal of said operating means and the photoelectric outputs of said third and fourth light detectors and for discriminating the presence of a foreign particle on the basis of a logic product of said output signal and said photoelectric outputs of said third and fourth light detectors.

2. Apparatus as set forth in claim 1, further comprising slit plate means for preventing stray light from impinging upon the light detectors.

3. Apparatus as set forth in claim 2, wherein said slit plate means comprises four slit plates adjacent to said light detectors, respectively, each of said light detectors having a condenser lens for guiding light from said surface of said substrate through a corresponding slit plate to the light detector, said slit plates being arranged at positions optically conjugated with said scanning line on the substrate with respect to the corresponding condenser lenses.

4. Apparatus as set forth in claim 3, wherein optical axes of the condenser lenses corresponding to said third and fourth light detectors define azimuth angles in the order of 15°-80° with respect to said scanning line.

5. Apparatus as set forth in claim 3, wherein optical axes of the condenser lenses define angles in the order of 10°-80° with respect to the surface of the substrate.

6. Apparatus as set forth in claim 3, wherein optical axes of the condenser lenses corresponding to said first and second light detectors define angles with respect to the surface of the substrate that are disposed symmetrically at opposite sides of said incident plane, and wherein optical axes of the condenser lenses corresponding to said third and fourth light detectors define angles with respect to the surface of the substrate that are also disposed symmetrically at opposite sides of said incident plane.

7. Apparatus as set forth in claim 3, wherein said condenser lenses are arranged substantially equidistant from said center of the scanning line and are positioned so that optical axes of said lenses intersect said scanning line at said center.

8. An apparatus as set forth in claim 1, wherein said second plane is positioned at an incident side of said first plane with respect to said light beam.

9. An apparatus for detecting foreign particles on a surface of a substrate covered with a transparent pellicle to protect said substrate, comprising:

a supplying means for supplying a light beam passing through said pellicle to the surface of said substrate from an oblique direction, said light beam forming a light spot repeatedly shifting along a scanning line on the surface of said substrate;

a shifting means for shifting said substrate to vary a position of said scanning line;

first and second light detectors arranged in a first plane which includes said scanning line and is perpendicular to the surface of said substrate and positioned symmetrically with respect to an incident plane of said light beam passing through a center of said scanning line, said first and second light detectors generating photoelectric outputs, respectively;

third and fourth light detectors arranged in a second plane parallel to said first plane and positioned symmetrically with respect to said incident plane, said third and fourth light detectors generating photoelectric outputs, respectively;

an operating means for receiving the photoelectric outputs of said first and second light detectors and for generating an output signal representing a logic sum of said photoelectric outputs; and a discriminating means for receiving the output signal of said operating means and the photoelectric outputs of said third and fourth light detectors and for discriminating the presence of a foreign particle on the basis of a logic product of said output signal and said photoelectric outputs of said third and fourth light detectors.

* * * * *